United States Patent [19]
Alnemri et al.

[11] Patent Number: 5,861,498
[45] Date of Patent: Jan. 19, 1999

[54] NUCLEOTIDES ENCODING IMMUNOPHILIN FKBP46 AND FRAGMENTS THEREOF

[75] Inventors: Emad S. Alnemri; Teresa Fernandes-Alnemri, both of Ambler; Gerald Litwack, Wynnewood, all of Pa.

[73] Assignee: Thomas Jefferson University, Philadelphia, Pa.

[21] Appl. No.: 741,134

[22] Filed: Oct. 31, 1996

Related U.S. Application Data

[60] Provisional application No. 60/007,163 Nov. 1, 1995.
[51] Int. Cl.$^6$ .................................................. C07H 21/04
[52] U.S. Cl. ........................................ 536/23.5; 435/320.1
[58] Field of Search ................................ 536/23.1, 23.5, 536/23.7, 24.3, 24.31, 24.32; 435/6, 320.1

[56] References Cited

U.S. PATENT DOCUMENTS 4,736,866  4/1988  Leder et al. .................................. 800/1
4,873,191 10/1989  Wagner et al. ....................... 435/172.1

OTHER PUBLICATIONS

Database Medline on STN; US National Library of Medicine, (Bethesda, MD, USA), No. 95074110, Alnemri et al., J. Bio. Chem., 269(49):30828–34, Sep. 1994.
Alnemri, et al., "Overexpressed full–length human BCL2 extends the survival of baculovirus–infected Sf9 insect cells", *Proc. Natl. Acad. Sci. USA*, 1992, 89, 7295–7299.
Alnemri, E.S. and Litwack, G., "The Steroid Binding Domain Influences Intracellular Solubility of the Baculovirus Overexpressed Glucocorticoid and Mineralocorticoid Receptors", *Biochem.*, 1993, 32, 5387–5393.
Alnemri, et al., "Overexpression, characterization, and purification of a recombinant mouse immunophilin FKBP–52 and identification of an associated phosphoprotein", *Proc. Natl. Acad. Sci. USA*, 1993, 90, 6839–6843.
Alnemri, et al., "Characterization and Purification of a Functional Rat Glucocorticoid Receptor Overexpressed in a Baculovirus System", *J. Biol. Chem.*, 1991, 266, 3925–3936.
Baskaran, B. and Rao, M.R.S., "Mammalian Spermatid Specific Protein, TP2, is a Zinc Metalloprotein with Two Finger Motifs", *Biochem. Biophys. Res. Commun.*, 1991, 179, 1491–1499.
Cole, K.D. and Kistler, S., "Nuclear Transition Protein 2 (TP2) of Mammalian Spermatids Has a Very Basic Carboxyl Terminal Domain", *Biochem. Biophys. Res. Commun.*, 1987, 147, 437–442.
Galat, et al., "A Rapamycin–Selective 25–kDa Immunophilin", *Biochem.*, 1992, 31, 2427–2434.
Gething, M.J. and Sambrook, J., "Protein folding in the cell", *Nature*, 1992, 355, 33–45.
Heitman, et al., "Targets for Cell Cycle Arrest by the Immunosuppressant Rapamycin in Yeast", *Science*, 1991, 253, 905–909.
Heitman, et al., "Proline Isomerases at the Crossroads of Protein Folding, Signal Transduction and Immunosuppression", *New Biol.*, 1992, 4, 448–460.
Harrison, R.K. and Stein, R.L., "Substrate Specificities of the Peptidyl Prolyl Cis–Trans Isomerase Activities of Cycophilin and FK–506 Binding Protein: Evidence for the Existence of a Family of Distinct Enzymes", *Biochem.*, 1990, 29, 3813–3816.
Jin, Y.J. and Burakoff, S.J., "The 25–kDa FK506–binding protein is localized in the nucleus and associates with casein kinase II and nucleolin", *Proc. Natl. Acad. Sci. USA*, 1993, 90, 7769–7773.
Johnson, P.F. and McKnight, S.L., "Eukaryotic Transcriptional Regulatory Proteins", *Annu. Rev. Biochem.*, 1989, 58, 799–839.
Kalderon, et al., "Sequence requirements for nuclear location of simian virus 40 large–T antigen", *Nature*, 1984, 311, 33–38.
Koltin, et al., "Rapamycin Sensitivity in *Saccharomyces cerevisiae*Is Mediated by a Peptidyl–Prolyl cis–trans Isomerase Related to Human FK506–Binding Protein", *Mol. Cell. Biol.*, 1991, 11, 1718–1723.
Liu, et al., "Calcineurin is a Common Target of Cyclophilin–Cyclosporin A and FKBP–FK506 Complexes", *Cell*, 1991, 66, 807–815.
Liu, et al., "Inhibition of T Cell Signaling by Immunophilin–Ligand Complexes Correlates with Loss of Calcineurin Phosphatase Activity", *Biochem.*, 1992, 31, 3896–3901.
Maki, et al., "Complementary DNA encoding the human T–cell FK506–binding protein, a peptidylprolyl cis–trans isomerase distinct from cyclophilin", *Proc. Natl. Acad. Sci. USA*, 1990, 87, 5440–5443.
Murre, et al., "A New DNA Binding and Dimerization Motif in Immunoglobulin Enhancer Binding, daughterless, MyoD, and myc Proteins", *Cell*, 1989, 56, 777–783.

(List continued on next page.)

Primary Examiner—Scott W. Houtteman
Attorney, Agent, or Firm—Woodcock Washburn Kurtz Mackiewicz & Norris, LLP

[57] ABSTRACT

A substantially pure protein, immunophilin FKBP46, is disclosed. An isolated nucleic acid molecule that comprises a nucleic acid sequence that encodes immunophillin FKBP46, is disclosed. An isolated nucleic acid molecule consisting of a nucleic acid sequence that encodes immunophillin FKBP46, or a fragment thereof having at least 10 nucleotides is disclosed. Recombinant expression vector comprising a nucleic acid sequence that encodes immunophillin FKBP46 and host cells comprising the recombinant expression vector are disclosed. Oligonucleotide molecule comprising a nucleotide sequence complimentary to a nucleic acid sequence that encodes immunophillin FKBP46 of at least 5 nucleotides are disclosed. Antibodies that binds to an epitope on FKBP46 are disclosed. Methods of identifying immunosuppressive drugs comprising the steps of contacting FKBP46 or a homologous protein derived from yeast with a test compound and determining whether the protein binds to the test compound are disclosed.

25 Claims, 3 Drawing Sheets

OTHER PUBLICATIONS

Park, et al., "PPIase Catalysis by Human FK506–binding Protein Proceeds Through a Conformational Twist Mechanism", *J. Biol. Chem.,* 1992, 267, 3316–3324.

Peattie, et al., "Expression and characterization of human FKBP52, an immunophilin that associates with the 90–kDa heat shock protein and is a component of steroid receptor complexes", *Proc. Natl. Acad. Sci. USA,* 1992, 89, 10974–10978.

Robbins, et al., "Two Interdependent Basic Domains in Nucleoplasmin Nuclear Targeting Sequence: Identification of a Class of Bipartite Nuclear Targeting Sequence", *Cell,* 1991, 64, 615–623.

Schreiber, "Chemistry and Biology of the Immunophilins and Their Immunosuppressive Ligands", *Science,* 1991, 251, 283–287.

Schreiber, "Immunophilin–Sensitive Protein Phosphatase Action in Cell Signaling Pathways", *Cell,* 1992, 70, 365–368.

Schreiber, S.L. and Crabtree, G.R., "The mechanism of action of cyclosporin A and FK506", *Immunol. Today,* 1992, 13, 136–142.

Shirakawa, et. al., "Primary Structure of Non–Histone Chromosomal Protein HMG2 Revealed by the Nucleotide Sequence", *Biochem.,* 1990, 29, 4419–4423.

Siekierka, et. al., "The Cytosolic–binding Protein for the Immunosuppressant FK–506 Is Both a Ubiquitous and Highly Conserved Peptidyl–Prolyl Cis–Trans Isomerase", *J. Biol. Chem.,* 1990, 265, 21011–21015.

Sigal, N.H. and Dumont, F.J., "Cyclosporin A, FK–506, and Rapamycin: Pharmacologic Probes of Lymphocyte Signal Transduction", *Annu. Rev. Immunol.,* 1992, 10, 519–560.

Stamnes, et al., "The Cyclophilin Homolog ninaA is a Tissue–Specific Integral Membrane Protein Required for the Proper Synthesis of a Subset of *Drosophila Rhodopsins",* *Cell,* 1991, 65, 219–227.

Standaert, et al., "Molecular cloning and overexpression of the human FK506–binding protein FKBP", *Nature,* 1990, 346, 671–674.

Tai, et al., "Association of a 50–Kilodalton Immunophilin with the Glucocorticoid Receptor Complex", *Science,* 1992, 256, 1315–1318.

Tai, et al., "P59 (FK506 Binding Protein 59) Interaction with Heat Shock Proteins is Highly Conserved and May Involve Proteins Other Than Steroid Receptors", *Biochem.,* 1993, 32, 8842–8847.

Van Duyne, et al., "Atomic Structure of FKBP–FK506, an Immunophilin–Immunosuppressant Complex", *Science,* 1991, 252, 839–842.

FIGURE 1

```
   1 GAATTCGGCACGAGCTTGATTTTGCCGCGTTTGAACGCATGCTGTGATCCACATTTGAAT    60
  61 AAAAGAAACCGGCAAAACTATTTTATTATTTAGTGTCGTAATAAACTTTCTTTTAAAGCC   120
   1                                            M  F  W  G  L  I  M    7
 121 GAATTATATCTATAGTTTGTTATAAATAAAAACGTCAAAATGTTTTGGGGACTTATTATG   180
   8  E  P  N  K  R  Y  T  Q  V  V  E  K  P  F  H  I  S  Q  A  A    27
 181 GAACCGAACAAACGGTACACCCAAGTGGTGGAGAAACCGTTCCACATCTCACAGGCAGCT   240
  28  M  D  I  S  T  G  D  N  D  P  C  Q  V  M  V  V  V  D  G  K    47
 241 ATGGACATCAGCACCGGAGACAATGATCCCTGCCAAGTTATGGTAGTAGTCGATGGCAAG   300
  48  N  F  L  V  C  T  L  Q  K  G  K  I  I  Q  V  P  L  D  L  Y    67
 301 AACTTCCTAGTGTGCACATTACAGAAGGGCAAGATTATCCAGGTGCCCTTGGACTTGTAT   360
  68  F  K  S  G  D  S  V  S  F  L  T  N  G  K  C  N  V  H  L  T    87
 361 TTCAAATCTGGAGATTCAGTTTCATTCTTGACAAATGGTAAATGCAATGTTCACTTGACT   420
  88  G  Y  L  D  P  E  F  E  E  D  L  E  D  E  E  E  A  E  E      107
 421 GGTTACCTTGATCCTGAGTTTGAGGAGGATTTGGAGGATGAGGAAGAGGCTGAAGAAGAA   480
 108  E  E  E  E  E  A  P  P  L  V  P  A  K  N [K  R  K] L  E  N   127
 481 GAGGAGGAGGAGGAGGCTCCACCTCTAGTGCCAGCTAAGAATAAGAGGAAACTCGAGAAT   540
 128  A  N  D  A  T  A  N [K  K  A  K] P  D  K  K  A  G  K  N  S   147
 541 GCCAATGATGCCACAGCTAACAAAAAGGCCAAGCCTGACAAGAAAGCTGGCAAGAACAGT   600
 148  A  P  A  A  E  S  D  S  D  D  D  D  E  D  Q  L  Q  K  F  L   167
 601 GCACCAGCAGCAGAAAGTGATTCAGATGACGATGATGAAGACCAGCTTCAAAAGTTCCTT   660
 168  D  G  E  D  I  D  T  D  E  N  D  E  S  F  K  M  N  T  S  A   187
 661 GACGGTGAAGATATAGACACTGATGAAAATGATGAATCATTCAAAATGAACACATCAGCT   720
 188  E  G  D  D  S  D  E  E  D  D  D  E  D  E  E  D  E  E  D  D   207
 721 GAAGGAGATGACAGTGATGAAGAGGATGATGATGAAGACGAAGAGGATGAAGAAGATGAT   780
 208  D  E  D  D  E  E  E  E  A  P [K  K  K  K] Q  P  A  A         227
 781 GATGAGGACGATGAAGAAGAGGAGGAAGCACCCAAGAAGAAGAAGAAACAGCCAGCCGCA   840
 228  E  Q  D  S  T  L  D  T  S  K  E  S  V  D  M  S  K  L  S  K   247
 841 GAGCAGGACTCAACACTGGACACAAGCAAGGAGTCTGTGGACATGTCCAAACTGTCCAAG   900
 248  S  Q [K  R  R  L  K  K  K] L  Q  Q  A  K  Q  Q  P  Q  V      267
 901 TCACAAGAGAAGGCTCAAGAAGAAGCTCCAACAACAAGCTAAACAACAGCCCTCAAGTC   960
 268  N  G  V  D [K  P  K] E  E  P  Q  Q  K  A  E [K  K  K] P      287
 961 AATGGAGTTGATAAGCCTAAGAAAGAGGAACCCCAACAGAAGGCTGAAAAGAAGAAGCCT  1020
 288  E  A  K  K  E  E  A  P  V  E [K  K  E  K] Q  I  A  G  G      307
1021 GAGGCCAAGAAAGAAGAGGCTCCAGTAGAGAAGAAAGAAAAGCAAATTGCTGGTGGT    1080
 308  V  S  I  E  D  L  K  V  G  S  G  P  V  A  K  A  G  K  V  V   327
1081 GTTTCTATTGAAGACCTCAAGGTCGGTTCTGGACCTGTTGCCAAGGCTGGCAAAGTTGTA  1140
 328  M  V  Y  Y  E  G  R  L  K  Q  N  N  K  F  D  N  C  V  K      347
1141 ATGGTTTACTACGAAGGTCGCCTTAAGCAAAACAACAAGATGTTTGACAACTGTGTGAAA  1200
 348  G  P  G  F  K  F  R  L  G  S  K  E  V  I  S  G  W  D  V  G   367
1201 GGACCTGGCTTCAAGTTCCGCCTAGGATCCAAGGAGGTCATCTCTGGCTGGGATGTAGGT  1260
 368  I  A  G  M  K  V  G  G  K  R  K  I  V  C  P  P  A  M  A  Y   387
1261 ATTGCTGGCATGAAGGTTGGAGGCAAGAGGAAGATCGTCTGCCCACCTGCAATGGCGTAT  1320
 388  G  A  K  G  S  P  P  V  I  P  P  N  S  T  L  V  F  E  V  D   407
1321 GGAGCCAAAGGATCACCTCCAGTCATCCCACCAAACTCAACTCTAGTATTTGAAGTTGAC  1380
 408  L  K  N  V  K                                                 412
1381 CTGAAGAATGTGAAATAAGTGAAATGTTGATGAATGTGCCAGTATGTCGAGAACTTGTTG  1440
1441 ATTTGCTTTAATTGAATGTTTATTGAAAGGTTGACATTGAATGCATGATTGTTGAAACAG  1500
1501 TTACAATGTGCTCTATCTGCAATAAGTTTATTTTGTGTGAATTAGAAGAGGTGCTACATA  1560
1561 TTGTGTAACATTATGATACTATTTCTTCAATCATATCTTGTTTTTCATATGAAAAATATC  1620
1621 TTTATTCTGAAATTACATAATTGTTTTTCTATTGAACATCAGTAAAATATTGCAGGTATA  1680
1681 CCACATTGTTGTCTACAGCATAAGTTGTCTTAAGTTAGTTCATAAGGATTTTACTGGACA  1740
1741 TGATAACTTAAATTCAGCTGCAGAATAAACCAAATTGTTCTAAAAAAATTTTGGTTTCTG  1800
1801 AAAAATATCCTGTCACTTTTACCCAAATTCTATTTCCGATAAAATATTAAATAAATGTTT  1860
1861 TTTTTTTAATAAAGTACCAATAGAATGAAGCCTCTGATGTAAATGTGTGACATCTATTTC  1920
1921 TGGTTAAGATAGTTATTAATTCCGACTATTATTATATAAGGTTATTTTACTAAGAAGTTT  1980
1981 TTCATGGAAGACTTTCCATAGTAAACCAGTATGCATTATACATGTAAGAGTAAAAGATAT  2040
2041 GTTTGAATTTTAATAAAAAACTAGACAATCATTCAGAGCATGGACTAATTTAAATTATTA  2100
2101 GTTCATGATGCAGAGTAACACTCAACAATGATTATCTAGTTTTTGGGACAAGCATAGTGTA  2160
2161 CTAGTCTTTGTCATCTGCATGTATTCCACAAACTGTTGGTATGACTAAGGTACTCTAATC  2220
2221 AACCAAATATTGTGAAATAAAAGTCAAGAAGTCTAAAAAAAAAAAAAAAAAAAAAACT    2280
2281 CGAG                                                             2284
```

FIGURE 2A

```
             1                                                          49
sFKBP46   KQIAGGVSIE DLKVGSG.PV AKACKVVMMY YEGPLKQNNK MFDNCVKGPG
mFKBP52   KQD.EGVLKV IKREGTGTET PMIGDRVFMH YTGMLLDGTK FDSSLDRKDK
hFKBP12   ....MGVDVE TISPGDGRTF PKRGQTCVVH YTGMLEDGKK FDSSRDRNKP 50                                                          99
sFKBP46   RKFPLGSKEV ISGWDVGIAG MKVGGKRKIV CRPAMAYGAK GSPPVIPPNS
mFKBP52   FSRDLGKQEV IKAWDIAVAT MKVGEVCHIT CKPEYAYGAA GSPPKIIPENA
hFKBP12   FKFMLGKQEV IRGWEEGVAQ MSVGQRAKLT ISPDYAYGAT GHPGIIPPHA 100       111
sFKBP46   TLVFEVDLKN VK
mFKBP52   TLVFEVELFE FK
hFKBP12   TLVFDVELLK LE
```

FIGURE 2B

```
  HMG2     85   KGKKKDPNAPKRPPSAFFLFCSEHRPKIKSEHPGL...SIGDTAKKLGEMW  132
                |  |||:|.|..   ..     : :  ..  ||:..| .:.: ||. .::
sFKBP46   219   KKKKKQPAAEQDSTLDTSKESVDMSKLSKSQKRRLKKKLQQQAKQQPQVN  268

HMG2    133   SEQSAKDKQPYEQKAAKLKEKYEKDIAAYRAKGKGEAG  170
                : :..:|..:|  :|||.|  ..  .|: |:   |:|  : :
sFKBP46   269   GVDKPKKEEP.QQKAEKKKPEAKKEEAPVEKKEKKQIA  305
```

NUCLEOTIDES ENCODING IMMUNOPHILIN FKBP46 AND FRAGMENTS THEREOF

ACKNOWLEDGEMENT OF GOVERNMENT RIGHTS

This invention was made with Government support under Grant A1 35035-01 from the National Institutes of Health. The Government has certain rights in this invention.

This application claims the benefit of U.S. Provisional Application No. 60/007,163 filed Nov. 1, 1995.

FIELD OF THE INVENTION

The invention relates to the identification and cloning of FKBP46, a novel Sf9 insect cell nuclear immunophilin that forms a protein kinase complex and to methods of making and using the same.

BACKGROUND OF THE INVENTION

Immunophilins are proteins that bind immunosuppressive drugs such as FK506, rapamycin, and cyclosporin A (Schreiber, S. L. (1991) *Science* 251, 283–287, which is incorporated herein by reference). Immunophilins that bind FK506 or rapamycin are known as FK binding proteins or FKBPs, and those that bind cyclosporin A are known as cyclophilins. Both FK506 and rapamycin are potent immunosuppressants that act by blocking specific intermediate steps in the signal transduction pathways that lead to T-cell activation (Schreiber, S. L. (1992) *Cell* 70, 365–368, Schreiber, S. L., and Crabtree, G. R. (1992) *Immunol. Today* 13, 136–142, Liu. J., et al. (1991) *Cell* 66, 807–815, and Sigal, N. H., and Dumont. F. J. (1992) *Annu. Rev. Immunol.* 10, 519–560, which are incorporated herein by reference). In T-lymphocytes, binding of FK506 to the well characterized FKBP12 results in the formation of a protein complex of FKBP12 and calcineurin leading to inactivation of calcineurin phosphatase activity (Liu, J., et al. (1992) *Biochemistry,* 31, 3896–3901, which is incorporated herein by reference) and subsequently inhibition of T-cell activation. Immunophilins also mediate the effects of immunosuppressive drugs in many cell types. For example, FK506 affects signal transduction in B lymphocytes and mast cells, whereas rapamycin inhibits proliferation of yeasts (Koltin, Y., et al. (1991) *Mol. Cell. Biol.* 11, 1718–1723 and Heitman, J., et al. (1991) Science 253, 905–909 which are incorporated herein by reference). Aside from the ability to interact with immunosuppressive drugs, the relevant physiological function and the endogenous ligands or regulators of immunophilins are not yet known. Because immunophilins are conserved in evolution and all known immunophilins possess peptidylprolyl isomerase or rotamase activity, it has been suggested that they may catalyze protein folding and trafficking in vivo and assembly of protein complexes (Gething, M. J., and Sambrook, J. (1992) *Nature* 355, 33–45 which is incorporated herein by reference). The Drosophila immunophilin ninaA has been shown to be essential for trafficking of one isoform of rhodopsin to the membrane in the retina (Stamnes, M. A., et al. (1991) *Cell* 65, 219–227 which is incorporated herein by reference). The newly discovered immunophilin FKBP52 is part of the glucocorticoid receptor (GR) complex (Tai, P. K., et al. (1992) *Science,* 256, 1315–1318 which is incorporated herein by reference) and other uncharacterized protein complexes (Tai, P. K., et al. (1993) *Biochemistry* 32, 8842–8847 which is incorporated herein by reference).

There is a need to identify immunophilin. There is a need to identify compounds that bind to immunophilins. There is a need to study and understand the mechanisms by which immunosuppressive drugs function and for reagents useful in such studies. There remains a need to identify new immunosuppressive drugs. There is a need for kits and methods of identifying such compounds. There is a need for isolated immunophilins, and for compositions and methods of producing and isolating immunophilins. There is a need to isolated proteins that are immunophilins. There is a need to isolated nucleic acid molecules that encode immunophilins.

SUMMARY OF THE INVENTION

The invention relates to substantially pure proteins that have amino acid sequences shown in SEQ ID NO:2.

The invention relates to isolated nucleic acid molecules that comprise nucleic acid sequences that encode a protein that has an amino acid sequence shown in SEQ ID NO:2.

The invention relates to isolated nucleic acid molecules that consist of SEQ ID NO:1 or a fragment thereof having at least 5 nucleotides.

The invention relates to a recombinant expression vector comprising the nucleic acid molecule that has a nucleotide sequence that comprises SEQ ID NO:1.

The invention relates to a host cell comprising a recombinant expression vector comprising the nucleic acid molecule that has a nucleotide sequence that comprises SEQ ID NO:1.

The invention relates to an oligonucleotide molecule comprising a nucleotide sequence complimentary to a nucleotide sequence of at least 5 nucleotides of SEQ ID NO:1.

The invention relates to isolated antibodies that bind to an epitope on SEQ ID NO:2.

The invention relates to methods of identifying compounds that bind to FKBP46.

The invention relates to methods of identifying compounds that bind to a protein isolated from yeast that is homologous to FKBP46.

BRIEF DESCRIPTION OF THE FIGURES

FIG. 1 shows the nucleotide and predicted amino acid sequence of the FKBP46 cDNA (SEQ ID NO:1 and SEQ ID NO:2). A cDNA encoding a full-length Sf9 FKBP46 was isolated from an Sf9 λ Uni-ZAP™ XR cDNA library. The length of this cDNA (2284) is consistent with the observed size of the FKBP46 mRNA (~2400 bp) by Northern blot analysis. The single long open reading frame begins with an ATG at position 160 (M-1) and terminates at TAA stop codon (underlined) at position 1396 (K-412). Two upstream in-frame nonsense codons (TAG) at positions 91 and 133 are also underlined. Five consensus polyadenylation signals at positions 1764, 1850, 1868, 2052, and 2237 are shown with brackets. Three EEAP and one Ap motifs (underlined in boldface) separate the distinct acidic, basic, and FKBP-like domains. Consensus bipartite nuclear targeting sequences within the first and second basic domains are boxed. An SV40 large T-antigen-like nuclear-targeting sequence is also present at the beginning of the second basic domain (shaded box).

FIGS. 2A and 2B show amino acid sequence comparison of the Sf9 FKBP46 with other proteins. FIG. 2A shows a colinear sequence alignment of the FKBP-like domains of the Sf9 FKBP46 (sFKBP46, amino acids 302–412), mouse FKBP52 (mFKBP52, amino acids 32–139), and human FKBP12 (hFKBP12, amino acids 1–108). The numbering indicates positions within the FKBP-like domain. Amino acids identical in all three sequences are boxed, and those identical or similar in at least two out of three positions are shaded. FIG. 2B shows colinear sequence alignment of the second basic domain of Sf9 FKBP46 with the porcine HMG2 DNA binding domain. The alignment in FIGS. 2A and 2B were made using Telnet 2.4.01 MacTCP program based on the evolutionary distance between the amino acids (gap weight, 3: gap length weight, 0.1).

In FIG. 3A, purified His-FKBP46 immobilized on $Ni^{2+}$ affinity resin was incubated with [$^3$H]dihydro-FK506 in the presence (completed) or absence of cold FK506. The numbers under each column represent different amounts of nuclear extracts in microliters from Sf9 cells—expressing His-FKBP46 bound to separate $Ni^{2+}$ affinity resins. Nuclear extracts from wild type (WT) baculovirus infected Sf9 cells (10 $\mu$l) were bound to $Ni^{2+}$ affinity resin and used as a control. The amount of radioactivity associated with each resin sample is represented in disintegrations/min. In FIG. 3B, time-dependant release of p-nitroanilide by chymotrypsin from trans N-succinyl-Ala-Leu-Pro-Phe-p-nitroanilide measured by absorbance at 400 nm. Curve A reflects the rate of release of p-nitroanilide in a reaction catalyzed by FKBP46. Curve B is the same as curve A but in the presence of 5 $\mu$M FK506. Curve C is the same but without FKBP46.

DETAILED DESCRIPTION OF THE INVENTION

Figure 3A:
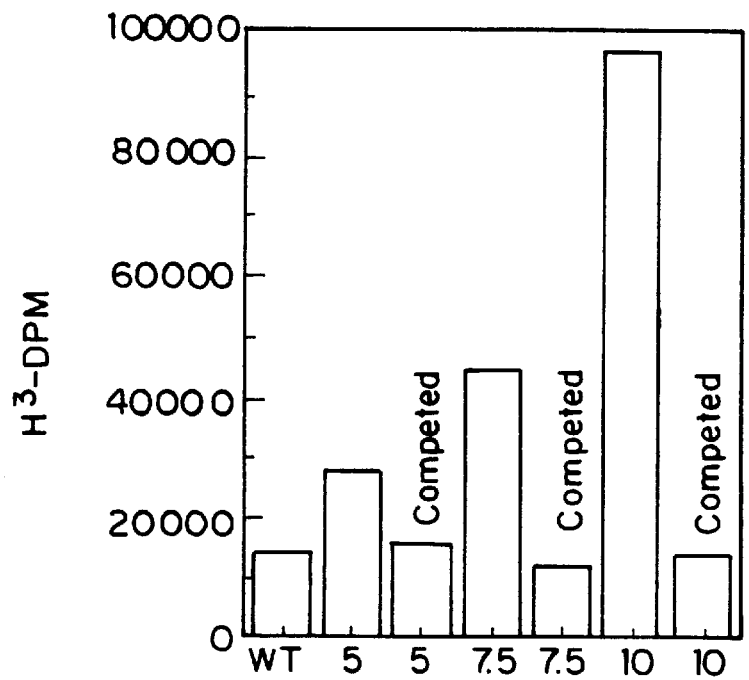
FIGS. 3A and 3B show FK506 binding and Peptidylprolyl cis-trans isomerase activities of FKBP46.

The discovery of FKBP46 provides the means to study immunosuppressive drugs that bind to it and to identify compounds that bind to it.

According to the present invention, FKBP46 may be used to screen compounds to identify those compounds that bind to it. Immunosuppressive drugs, such as FK506 and rapamycin, are useful in the treatment of individuals who have undergone organ or tissue transplantation procedures. The present invention provides the means for identification of additional immunosuppressive drugs. Methods and kits are provided for screening compounds for FKBP46 binding. Reagents useful in the method and kits as well as reagents for producing such reagents are provided. The nucleotide sequences that encode FKBP46 are disclosed herein and allow for the production of pure protein, the design of probes which specifically hybridize to nucleic acid molecules that encode FKBP46 and antisense compounds to inhibit transcription of FKBP46. Anti-FKBP46 antibodies are provided. Anti-FKBP46 antibodies may be inhibitor FKBP46 from binding to FK506 and/or rapamycin and may also be used in methods of isolating pure FKBP46 and methods of inhibiting FKBP46 activity.

The present invention provides substantially purified FKBP46 which has amino acid sequences consisting of SEQ ID NO:2. FKBP46 can be isolated from natural sources, produced by recombinant DNA methods or synthesized by standard protein synthesis techniques.

Antibodies which specifically bind to FKBP46 may be used to purify the protein from natural sources using well known techniques and readily available starting materials. Such antibodies may also be used to purify FKBP46 from material present when producing the protein by recombinant DNA methodology. As used herein, the term "antibody" is meant to refer to complete, intact antibodies, and Fab fragments and F(ab)$_2$ fragments thereof. Complete, intact antibodies include monoclonal antibodies such as murine monoclonal antibodies, chimeric antibodies and humanized antibodies. Antibodies that bind to an epitope which is present on FKBP46 are useful to isolate and purify FKBP46 from both natural sources or recombinant expression systems using well known techniques such as affinity chromatography. Such antibodies are useful to detect the presence of such protein in a sample and to determine if cells are expressing the protein.

The production of antibodies and the protein structures of complete, intact antibodies, Fab fragments and F(ab)$_2$ fragments and the organization of the genetic sequences that encode such molecules are well known and are described, for example, in Harlow, E. and D. Lane (1988) ANTIBODIES: *A Laboratory Manual,* Cold Spring Harbor Laboratory, Cold Spring Harbor, N.Y. which is incorporated herein by reference. Briefly, for example, FKBP46 or an immunogenic fragment thereof is injected into mice. The spleen of the mouse is removed, the spleen cells are isolated and fused with immortalized mouse cells. The hybrid cells, or hybridomas, are cultured and those cells which secrete antibodies are selected. The antibodies are analyzed and, if found to specifically bind to FKBP46, the hybridoma which produces them is cultured to produce a continuous supply of antibodies.

Using standard techniques and readily available starting materials, a nucleic acid molecule that encodes FKBP46 may be isolated from a cDNA library, using probes or primers which are designed using the nucleotide sequence information disclosed in SEQ ID NO:1. The present invention relates to an isolated nucleic acid molecule that comprises a nucleotide sequence that encodes FKBP46 that comprises the amino acid sequence of SEQ ID NO:2. In some embodiments, the nucleic acid molecules comprise the nucleotide sequence that consists of the coding sequence in SEQ ID NO:1. In some embodiments, the nucleic acid molecules consist of the nucleotide sequence set forth in SEQ ID NO:1. The isolated nucleic acid molecules of the invention are useful to prepare constructs and recombinant expression systems for preparing FKBP46.

A cDNA library may be generated by well known techniques. A cDNA clone which contains one of the nucleotide sequences set out is identified using probes that comprise at least a portion of the nucleotide sequence disclosed in SEQ ID NO:1. The probes have at least 16 nucleotides, preferably 24 nucleotides. The probes are used to screen the cDNA library using standard hybridization techniques. Alternatively, genomic clones may be isolated using genomic DNA from any human cell as a starting material. The present invention relates to isolated nucleic acid molecules that comprise a nucleotide sequence identical or complementary to a fragment of SEQ ID NO:1 which is at least 10 nucleotides. In some embodiments, the isolated nucleic acid molecules consist of a nucleotide sequence identical or complementary to a fragment of SEQ ID NO:1 which is at least 10 nucleotides. In some embodiments, the isolated nucleic acid molecules comprise or consist of a nucleotide sequence identical or complementary to a fragment of SEQ ID NO:1 which is 15–150 nucleotides. In some embodiments, the isolated nucleic acid molecules comprise or consist of a nucleotide sequence identical or complementary to a fragment of SEQ ID NO:1 which is 15–30 nucleotides. Isolated nucleic acid molecules that comprise or consist of a nucleotide sequence identical or complementary to a fragment of SEQ ID NO:1 which is at least 10 nucleotides are useful as probes for identifying genes and cDNA sequence having SEQ ID NO:1, PCR primers for amplifying genes and cDNA having SEQ ID NO:1, and antisense molecules for inhibiting transcription and translation of genes and cDNA, respectively, which encode FKBP46 having the amino acid sequence of SEQ ID NO:2.

The cDNA that encodes FKBP46 may be used as a molecular marker in electrophoresis assays in which cDNA from a sample is separated on an electrophoresis gel and FKBP46 isoform probes are used to identify bands which hybridize to such probes. Specifically, SEQ ID NO:1 or portions thereof, may be used as a molecular marker in electrophoresis assays in which cDNA from a sample is separated on an electrophoresis gel and FKBP46 specific probes are used to identify bands which hybridize to them, indicating that the band has a nucleotide sequence complementary to the sequence of the probes. The isolated nucleic acid molecule provided as a size marker will show up as a positive band which is known to hybridize to the probes and thus can be used as a reference point to the size of cDNA that encodes FKBP46. Electrophoresis gels useful in such an assay include standard polyacrylamide gels as described in Sambrook et al., *Molecular Cloning a Laboratory Manual,* Second Ed. Cold Spring Harbor Press (1989) which is incorporated herein by reference.

The nucleotide sequences in SEQ ID NO:1 may be used to design probes, primers and complimentary molecules which specifically hybridize to the unique nucleotide sequences of FKBP46. Probes, primers and complimentary molecules which specifically hybridize to nucleotide sequence that encodes FKBP46 may be designed routinely by those having ordinary skill in the art.

The present invention also includes labelled oligonucleotides which are useful as probes for performing oligonucleotide hybridization methods to identify FKBP46. Accordingly, the present invention includes probes that can be labelled and hybridized to unique nucleotide sequences that encode FKBP46. The labelled probes of the present invention are labelled with radiolabelled nucleotides or are otherwise detectable by readily available nonradioactive detection systems. In some preferred embodiments, probes comprise oligonucleotides consisting of between 10 and 100 nucleotides. In some preferred, probes comprise oligonucleotides consisting of between 10 and 50 nucleotides. In some preferred, probes comprise oligonucleotides consisting of between 12 and 20 nucleotides. The probes preferably contain nucleotide sequence completely identical or complementary to a fragment of a unique nucleotide sequences of FKBP46α and FKBP46β.

PCR technology is practiced routinely by those having ordinary skill in the art and its uses in diagnostics are well known and accepted. Methods for practicing PCR technology are disclosed in "PCR Protocols: A Guide to Methods and Applications", Innis, M. A., et al. Eds. Academic Press, Inc. San Diego, Calif. (1990) which is incorporated herein by reference. Applications of PCR technology are disclosed in "Polymerase Chain Reaction" Erlich, H. A., et al., Eds. Cold Spring Harbor Press, Cold Spring Harbor, N.Y. (1989) which is incorporated herein by reference. Some simple rules aid in the design of efficient primers. Typical primers are 18–28 nucleotides in length having 50% to 60% g+c composition. The entire primer is preferably complementary to the sequence it must hybridize to. Preferably, primers generate PCR products 100 basepairs to 2000 base pairs. However, it is possible to generate products of 50 base pairs to up to 10 kb and more.

PCR technology allows for the rapid generation of multiple copies of nucleotide sequences by providing 5' and 3' primers that hybridize to sequences present in a nucleic acid molecule, and further providing free nucleotides and an enzyme which fills in the complementary bases to the nucleotide sequence between the primers with the free nucleotides to produce a complementary strand of DNA. The enzyme will fill in the complementary sequences adjacent to the primers. If both the 5' primer and 3' primer hybridize to nucleotide sequences on the complementary strands of the same fragment of nucleic acid, exponential amplification of a specific double-stranded product results. If only a single primer hybridizes to the nucleic acid molecule, linear amplification produces single-stranded products of variable length.

One having ordinary skill in the art can isolate the nucleic acid molecule that encode FKBP46 and insert it into an expression vector using standard techniques and readily available starting materials.

The present invention relates to a recombinant expression vector that comprises a nucleotide sequence that encodes FKBP46 that comprises the amino acid sequence of SEQ ID NO:2. As used herein, the term "recombinant expression vector" is meant to refer to a plasmid, phage, viral particle or other vector which, when introduced into an appropriate host, contains the necessary genetic elements to direct expression of the coding sequence that encodes the FKBP46 isoforms of the invention. The coding sequence is operably linked to the necessary regulatory sequences. Expression vectors are well known and readily available. Examples of expression vectors include plasmids, phages, viral vectors and other nucleic acid molecules or nucleic acid molecule containing vehicles useful to transform host cells and facilitate expression of coding sequences. In some embodiments, the recombinant expression vector comprises the nucleotide sequence set forth in SEQ ID NO:1. The recombinant expression vectors of the invention are useful for transforming hosts to prepare recombinant expression systems for preparing FKBP46.

The present invention relates to a host cell that comprises the recombinant expression vector that includes a nucleotide sequence that encodes FKBP46 that comprises SEQ ID NO:1. In some embodiments, the host cell comprises a recombinant expression vector that comprises SEQ ID NO:1. Host cells for use in well known recombinant expression systems for production of proteins are well known and readily available. Examples of host cells include bacteria cells such as *E. coli,* yeast cells such as *S. cerevisiae,* insect cells such as *S. frugiperda,* non-human mammalian tissue culture cells chinese hamster ovary (CHO) cells and human tissue culture cells such as HeLa cells.

The present invention relates to a transgenic non-human mammal that comprises the recombinant expression vector that comprises a nucleic acid sequence that encodes FKBP46 that comprises the amino acid sequence of SEQ ID NO:2. Transgenic non-human mammals useful to produce recombinant proteins are well known as are the expression vectors necessary and the techniques for generating transgenic animals. Generally, the transgenic animal comprises a recombinant expression vector in which the nucleotide sequence that encodes FKBP46 is operably linked to a mammary cell specific promoter whereby the coding sequence is only expressed in mammary cells and the recombinant protein so expressed is recovered from the animal's milk. In some embodiments, the coding sequence that encodes FKBP46 is SEQ ID NO:1.

In some embodiments, for example, one having ordinary skill in the art can, using well known techniques, insert such DNA molecules into a commercially available expression vector for use in well known expression systems. For example, the commercially available plasmid pSE420 (Invitrogen, San Diego, Calif. ) may be used for production of collagen in *E. coli*. The commercially available plasmid pYES2 (Invitrogen, San Diego, Calif.) may, for example, be used for production in *S. cerevisiae* strains of yeast. The commercially available MAXBAC™ complete baculovirus expression system (Invitrogen, San Diego, Calif.) may, for example, be used for production in insect cells. The commercially available plasmid pcDNA I (Invitrogen, San Diego, Calif.) may, for example, be used for production in mammalian cells such as Chinese Hamster Ovary cells. One having ordinary skill in the art can use these commercial expression vectors and systems or others to produce FKBP46 using routine techniques and readily available starting materials. (See e.g., Sambrook et al., *Molecular Cloning a Laboratory Manual*, Second Ed. Cold Spring Harbor Press (1989) which is incorporated herein by reference.) Thus, the desired proteins can be prepared in both prokaryotic and eukaryotic systems, resulting in a spectrum of processed forms of the protein.

One having ordinary skill in the art may use other commercially available expression vectors and systems or produce vectors using well known methods and readily available starting materials. Expression systems containing the requisite control sequences, such as promoters and polyadenylation signals, and preferably enhancers, are readily available and known in the art for a variety of hosts. See e.g., Sambrook et al., *Molecular Cloning a Laboratory Manual*, Second Ed. Cold Spring Harbor Press (1989).

A wide variety of eukaryotic hosts are also now available for production of recombinant foreign proteins. As in bacteria, eukaryotic hosts may be transformed with expression systems which produce the desired protein directly, but more commonly signal sequences are provided to effect the secretion of the protein. Eukaryotic systems have the additional advantage that they are able to process introns which may occur in the genomic sequences encoding proteins of higher organisms. Eukaryotic systems also provide a variety of processing mechanisms which result in, for example, glycosylation, carboxy-terminal amidation, oxidation or derivatization of certain amino acid residues, conformational control, and so forth.

Commonly used eukaryotic systems include, but is not limited to, yeast, fungal cells, insect cells, mammalian cells, avian cells, and cells of higher plants. Suitable promoters are available which are compatible and operable for use in each of these host types as well as are termination sequences and enhancers, e.g. the baculovirus polyhedron promoter. As above, promoters can be either constitutive or inducible. For example, in mammalian systems, the mouse metallothionein promoter can be induced by the addition of heavy metal ions.

The particulars for the construction of expression systems suitable for desired hosts are known to those in the art. Briefly, for recombinant production of the protein, the DNA encoding the polypeptide is suitably ligated into the expression vector of choice. The DNA is operably linked to all regulatory elements which are necessary for expression of the DNA in the selected host. One having ordinary skill in the art can, using well known techniques, prepare expression vectors for recombinant production of the polypeptide.

The expression vector including the DNA that encodes the FKBP46 isoform is used to transform the compatible host which is then cultured and maintained under conditions wherein expression of the foreign DNA takes place. The protein of the present invention thus produced is recovered from the culture, either by lysing the cells or from the culture medium as appropriate and known to those in the art. One having ordinary skill in the art can, using well known techniques, isolate FKBP46 that is produced using such expression systems. The methods of purifying FKBP46 from natural sources using antibodies which specifically bind to FKBP46 as described above, may be equally applied to purifying FKBP46 produced by recombinant DNA methodology.

Examples of genetic constructs include FKBP46 coding sequence operably linked to a promoter that is functional in the cell line into which the constructs are transfected. Examples of constitutive promoters include promoters from cytomegalovirus or SV40. Examples of inducible promoters include mouse mammary leukemia virus or metallothionein promoters. Those having ordinary skill in the art can readily produce genetic constructs useful for transfecting with cells with DNA that encodes FKBP46 from readily available starting materials. Such gene constructs are useful for the production of FKBP46.

In some embodiments of the invention, transgenic non-human animals are generated. The transgenic animals according to the invention contain SEQ ID NO:1 under the regulatory control of a mammary specific promoter. One having ordinary skill in the art using standard techniques, such as those taught in U.S. Pat. No. 4,873,191 issued Oct. 10, 1989 to Wagner and U.S. Pat. No. 4,736,866 issued Apr. 12, 1988 to Leder, both of which are incorporated herein by reference, can produce transgenic animals which produce FKBP46. Preferred animals are rodents, particularly rats and mice, and goats.

In addition to producing these proteins by recombinant techniques, automated peptide synthesizers may also be employed to produce FKBP46. Such techniques are well known to those having ordinary skill in the art and are useful if derivatives which have substitutions not provided for in DNA-encoded protein production.

According to one aspect of the invention, compounds may be screened to identify compounds that bind to FKBP46. Immunosuppressive drugs FK506 and rapamycin both bind to FKBP46. In addition to the FKBP46 isolated from Sf9 cells, a homologous protein derived from yeast may also be used in such methods. The homologous protein is disclosed as SEQ ID NO:6. The nucleotide sequence of the cDNA encoding this protein is shown in SEQ ID NO:5 and in GenBank Accession #:sc8248.gb_new.

According to the present invention, compounds may be identified that bind to FKBP46 (SEQ ID NO:2) and/or the homologous yeast protein (SEQ ID NO:6). Such compounds are useful as immunosuppressive agents useful in treating transplant and tissue graft patients. Compounds which bind to FKBP46 include the immunosuppressive agents FK506 and rapamycin. The use of these immunosuppressive agents and others which have similar binding properties are well known and can be readily optimized by those having ordinary skill in the art.

To screen and identify agents which bind to FKBP46 and the homologous yeast protein, the protein is contacted with a test compound and evaluated to determine whether or not the protein and the test compound are bound to each other.

In some embodiments, the test compound is immobilized to a solid support and the protein, SEQ ID NO:2 or SEQ ID NO:6 for example, is contacted to the solid support. After washing to remove any unbound protein, the detection of the protein to the solid support indicates the protein is bound to the test compound on the solid support. The protein may be detected by labelling it and detecting the label or by contacting the solid support with a detectable antibody that binds to the protein.

Examples of labels for making proteins such as SEQ ID NO:2 or SEQ ID NO:6 or antibodies such as anti-SEQ ID NO:2 antibodies or anti-SEQ ID NO:6 antibodies detectable include avidin-biotin peroxidase (ABC), immunoalkaline phosphatase anti-alkaline phosphatase (APAAP), streptavadin peroxidase, streptavadin alkaline phosphate, glucose oxidase, fluorescein conjugates and immunogold.

In some embodiments, the protein, SEQ ID NO:2 or SEQ ID NO:6 for example, is immobilized to a solid support and the test compound is contacted to the solid support. After washing to remove any unbound test compound, the solid support is evaluated to detect the test compound bound to the protein. In some embodiments of the invention, the preferred concentration of test compound is between 1 $\mu$M and 500 $\mu$M. A preferred concentration is 10 $\mu$M to 100 $\mu$M. In some preferred embodiments, it is desirable to use a series of dilutions of test compounds.

Kits are included which comprise containers with reagents necessary to screen test compounds. Such kits include FKBP46 and/or a nucleic acid molecule that encodes FKBP46, or the homologous yeast protein and/or a nucleic acid molecule that encodes the homologous yeast protein and instructions for performing the assay. Kits may include FK506, rapamycin or antibodies that bind to FKBP46 or the homologous yeast protein. Antibodies may compete with FK506 or rapamycin to bind to FKBP46 or the homologous yeast protein or they may bind to epitopes not involved in FKBP46 or homologous yeast protein interactions with FK506 and rapamycin. Antibodies are preferably labelled to detect whether or not they are bound to the FKBP46 or the homologous yeast protein. Combinatorial libraries may be screened to identify compounds that compete with antibodies or FK506 or rapamycin to bind with FKBP46 or the homologous yeast protein.

According to one embodiment, combinatorial libraries of compounds that are disposed on a solid substrate are first contacted with FKBP46 or the homologous yeast protein and antibodies that bind to epitopes not involved in FKBP46 interactions with FK506 and rapamycin or homologous yeast protein interactions with FK506 and rapamycin. After washing all reagents not bound to the compounds on the solid substrate, the presence of antibodies indicates that the FKBP46 or homologous yeast protein binds with a compound in the library.

It has been discovered that FKBP46 is a substrate for Caspase-1, a novel Sf9 insect cell protease that is activated in apoptosis. The processing of FKBP46 may be involved in cell death.

EXAMPLE

Example 1

Cloning of the Sf9 Immunophilin FKBP46—An Sf9 λ Uni-ZAP™XR cDNA library was constructed from Sf9 mRNA as described by the manufacturer (Stratagene). The cDNA library was screened with a 200-bp partial cDNA probe generated by PCR using two degenerate oligonucleotide primers. These primers were derived from the N terminus and an internal amino acid sequence of the 59-kDa phosphoprotein (Alnemri, E. S., et al. (1993) *Proc. Natl. Acad. Sci. U.S.A.* 90, 6839–6843 which is incorporated herein by reference). Several cDNA clones were isolated and then rescued from the λ Zap phage clones into the Bluescript plasmid vector. The plasmid clones were characterized by restriction enzyme analysis and nucleotide sequencing.

Construction of Recombinant Transfer Vectors and Recombinant Baculoviruses—The Sf9 FKBP46 cDNA was excised from the Bluescript vector as a 1.7-kilobase pair cDNA fragment with DraI and PstI restriction enzymes and subcloned into a SmaI/PstI-cut pVL1393 to generate the recombinant transfer vector pVL-FKBP46. The cDNA fragment contains 45 bp of untranslated 5' sequence, the entire open reading frame, and 367 bp of untranslated 3' sequence. To produce an FHBP46 with a 6-histidine tag at its N terminus, the FKBP46 cDNA was subcloned into an EcoRI/PstI-cut pVL1393-His6 vector. The ATG start site of the FKBP46 cDNA was modified to include an EcoRI site in frame with the $(His)_6$ tag sequence by PCR. This was achieved using an EcoRI-containing primer (primer 1, 5'-CCGGAATTCTGTTTTGGGGACTTATTATGG-3' SEQ ID NO:3) and a second primer downstream of the XhoI site at position +373 relative to the ATG start site. The pVL-$His_6$-tFKBP46 contains a truncated FKBP46 cDNA that lacks the entire coding sequence of the C-terminal FK binding domain. The truncated cDNA was generated by PCR using primer 1 and a stop codon-containing complimentary primer (primer 2, 5'-CAGAACCGACCTTGAGGTCTTA-3' SEQ ID NO:4) located at +931 to +953 relative to the ATG start site. The sequences of all PCR-generated cDNAs were confirmed by automated sequencing. The pVL-TP2 transfer vector was generated from the pVL-$His_6$-FKBP52, which contains the GenBank cDNA X17068, which is incorporated herein by reference. The $His_6$-FKBP52 sequence was removed with BamHI/NcoI, and both ends of the transfer vector were blunted and relegated. The NcoI site is at the ATG start site of the mouse TP2 cDNA. All recombinant baculoviruses were produced as described previously (Alnemri, E. S., et al. (1991) *J. Biol. Chem.* 266, 3925–3936 and Summers, M. D., and Smith, G. E. (1987) *Tex. Agric. Exp. Stn. Bull.* 1555 which are incorporated herein by reference).

Preparation of Antibodies and Immunoblotting—The associated phosphoprotein (FKBP46) was purified to complete homogeneity and then fractionated by SDS-PAGE. The FKBP46 band was visualized by incubation of the gel in a solution of 4M sodium acetate, excised from the gel, and then homogenized with Freund's complete adjuvant. An estimated 300 $\mu$g of this protein was injected into two rabbits. The rabbits were boosted 2 times with the same antigen, and then antisera were collected from each rabbit. The polyclonal antisera were tested using Western blot analysis as described previously (Alnemri, E. S., et al. (1992) *Proc. Natl. Acad. Sci. U.S.A.* 89, 7295–7299 which is incorporated herein by reference).

Binding of FKBP46 to DNA Cellulose—Recombinant His-FKBP46 was extracted from nuclei of Sf9 cells ($2 \times 10^7$ cells) infected with the recombinant baculovirus AcNPV-His-FKBP46 at 48 h postinfection. Nuclei were prepared by lysing the cells in Hepes/Nonidet P-40 buffer as described previously (Alnemri, E. S., and Litwack, G. (1993) *Biochemistry* 32, 5387–5393 which is incorporated herein by reference). The nuclei were extracted with 0.5 ml of nuclei extraction buffer (20 mM Hepes, pH 7.4, 5 mM KCl, 0.5 mM $MgCl_2$, 0.5 mM dithiothreitol, 0.6M NaCl) on ice for 15 min with occasional vortexing and centrifuged at 16,000×g for 15 min. The supernatant was collected and then diluted 6-fold with the same extraction buffer without NaCl to bring the NaCl concentration to 0.1M. The diluted extract was centrifuged at 16,000×g for 10 min to remove insoluble material. Triton X-100 was then added to the extract to a final concentration of 0.1%. Recombinant truncated His-tFKBP46, which lacks the entire FKBP-like domain, was extracted from Sf9 cells infected with the recombinant baculovirus AcNPV-His-tFKBP46 at 48 h postinfection. Cytosolic extract containing the truncated His-tFKBP46 was prepared by lysing the cells ($2 \times 10^7$ cells) in 0.5 ml of hypotonic lysis buffer (20 mM Hepes, pH 7.4, 5 mM KCl, 0.5 mM $MgCl_2$, 0.5 mM dithiothreitol) by freeze thawing twice. The cytosolic extract was obtained after centrifugation at 16,000×g for 15 min. The extract was diluted 6-fold as above, and NaCl and Triton X-100 were added to the extract to final concentrations of 0.1M and 0.1%, respectively. Half of the nuclear and half of the cytosolic extracts (1.5 ml each) were mixed with two aliquots (0.5 ml, packed matrix) of hydrated DNA cellulose (Sigma), respectively, and allowed to bind for 3 h on ice. Each DNA cellulose matrix was washed 3 times with washing buffer (20 mM Hepes, pH 7.4, 2 mM $MgCl^2$, 0.5% Triton X-100) and then divided into four portions. The DNA cellulose portions were eluted with 0.6, 0.3, 0.15, and 0.075M NaCl in Hepes buffer, respectively. Equal amounts of Laemmli sample buffer were then added to each eluent and to each DNA cellulose portion, and the proteins were analyzed by SDS-PAGE and Western blotting.

[$^3$H]Dihydro-FK506 Binding Assay—Aliquots of purified His-FKBP46 immobilized on $Ni^{2+}$ affinity resin were incubated in 50 µl of 50 mM HEPES, pH 7.4, 125 mM KCl, and 50 nM [$^3$H]dihydro-FK506 (49.1 Ci/mmol) in the presence or absence of 5000-fold excess of cold FK506 on ice for 18 h. The resin samples were washed 3 times with the same buffer above without FK506 and then counted by scintillation counting. Aliquots of mock-purified wild type nuclear extract immobilized on $Ni^{2+}$ affinity resins were used as controls.

Peptidylprolyl cis-trans Isomerase Assay—Peptidylprolyl isomerase activity of FKBP46 was assayed as described previously (Harrison, R. K., and Stein, R. L. (1990) *Biochemistry* 29, 3813–3816 and Park, S. T., et al. (1992) *J. Biol. Chem.* 267, 3316–3324) with some modifications. His-FKBP46 (100 nM final) was incubated with the peptide substrate N-succinyl-Ala-Leu-Pro-Phe-p-nitroanilide (75 µM final) (Bachem, Switzerland) at 15° C. for 15 min. The reaction was started by the addition of chymotrypsin (100 µg/ml final) (Sigma), and the release of p-nitroanilide by chymotrypsin was measured by recording the increase in absorbance at 400 nm using a Perkin Elmer λ 3B spectrophotometer connected to a chart recorder.

Cloning and Sequence and Structural Domain Analyses of an Sf9 Immunophilin—In Sf9 cells, overexpression of a recombinant mouse FKBP52 resulted in the expression of the majority of this protein in the nucleus and its association with a 59-kDa nuclear phosphoprotein. The associated 59-kDa phosphoprotein was purified to complete homogeneity, and partial amino acid sequences were obtained from its N terminus and several cyanogen bromide-generated peptides. Using two degenerate oligonucleotides corresponding to the protein N terminus and one internal peptide sequence, a 200-bp partial cDNA sequence was amplified with the PCR from total Sf9 RNA. An Sf9 λ ZAP cDNA library was constructed and then screened using the 200-bp cDNA as a probe. Several cDNA clones were isolated and characterized by restriction enzyme analysis. One of these clones, which spans 2284 bp, was sequenced (SEQ ID NO:1 and FIG. 1).

The open reading frame, starting with an ATG at position 160 and terminating with a stop codon at position 1396, encodes a polypeptide of 412 amino acids. The presence of in frame stop codons at positions 91 and 133 and the agreement between the deduced and the actual N-terminal amino acid sequences suggests that the full-length coding sequence of the 59-kDa phosphoprotein had been cloned.

The predicted amino acid sequence revealed that the protein is highly charged and is divided into several distinct structural domains. These domains include four alternating acidic and basic domains encompassing amino acids 1–302 followed by a C-terminal FKBP-like domain of 110 amino acids (FIG. 1). The second acidic domain (amino acids 150–218), which is longer than the first acidic domain (amino acids 91–114), contains an uninterrupted stretch of polyglutamic/aspartic acid residues of 24 amino acids. Such polyacidic stretches are thought to be involved in protein-protein interaction. In nuclear proteins, these acidic stretches may allow interaction with positively charged nuclear proteins such as histones and transcription factors. The presence of two basic domains is another important feature of the primary structure of this protein. In nuclear proteins, basic domains may have roles in nuclear targeting and DNA binding.

A homology search of the two basic domains identified several potential nuclear targeting signals. One bipartite nuclear targeting signal (Robbins, J., et al. (1991) *Cell* 64, 615–623 which is incorporated herein by reference) (amino acids 122–138) was identified within the first basic domain. Within the second basic domain, a large T-antigen nuclear targeting signal (Kalderon, D., et al. (1984) *Nature* 311, 33–38, which is incorporated herein by reference) and two to three bipartite signals were also identified (FIG. 1).

The presence of these signals supports our biochemical and immunological localization of this protein to the nucleus.

The most striking feature of this protein is the primary structure of its 110 amino acids at the C terminus. The C terminus of this protein has significant homology to the FKBP-like domains of all known immunophilins, which bind immunosuppressive drugs rapamycin and FK506 (FKBPs) (Heitman, J., et al. (1992) *New Biol.* 4, 448–460 which is incorporated herein by reference). As illustrated in FIG. 2A, the FKBP-like domain of this protein (sFKBP46) shares about 41–45% sequence identity with those of the human FKBP12 (hFKBP12) (Maki, N., et al. (1990) *Proc. Natl. Acad. Sci. U.S.A.* 87, 5440–5443 and Standaert, R. F., et al. (1990) Nature 346, 671–674 which are incorporated herein by reference) and the mouse FKBP52 (mFKBP52) (Peattie, D. A., et al. (1992) *Proc. Natl. Acad. Sci. U.S.A.* 89, 10974–10978), respectively. Based on its calculated $M_r$ (~45,800) and the presence of the FKBP-like domain, this new protein will henceforth be referred to as FKBP46.

The only nuclear FKBP that possesses a DNA binding ability is FKBP25 (Jin, Y. J., and Burakoff, S. J. (1993) *Proc. Natl. Acad. Sci. U.S.A.* 90, 7769–7773 which is incorporated herein by reference). Like FKBP25, FKBP46 might be a DNA binding protein. A DNA binding domain may exist within the FKBP46 second basic domain. A colinear alignment of amino acids 219–305 of FKBP46 with the porcine HMG2 DNA binding domain (Shirakawa, H., et al. (1990) *Biochemistry* 29, 4419–4423 which is incorporated herein by reference) (amino acids 85–170) revealed significant sequence and structural homology (26% identity and 47% similarity) (FIG. 2B). As predicted by Chou and Fasman analysis. The FKBP46 second basic domain has a high potential to form α-helices. Such α-helices are characteristic structures that occur in many transcription factors and DNA binding proteins (Murre, C., et al. (1989) *Cell* 56, 777–783 and Johnson, P. F., and McKnight, S. L. (1989) *Annu. Rev. Biochem.* 58, 799–839 which are incorporated herein by reference). Another important feature of the FKBP46 sequence is the presence of an EEAP motif at the boundaries of each structural domain (FIG. 1).

Nuclear Localization and Overexpression of the Sf9 FKBP46—To further characterize FKBP46, a polyclonal antibody was raised in rabbits against the purified protein. In addition, the FKBP46 cDNA was used to construct recombinant baculoviruses that encode a recombinant FKBP46 and a recombinant His-FKBP46 that has a $(His)_6$ tag on its N terminus. Western blot analysis of nuclear and cytosolic extracts from wild type virus-infected or uninfected Sf9 cells revealed that the endogenous FKBP46 is expressed in the nucleus. Cytosolic (C) and nuclear (N) extracts from wild type (WT) baculovirus-infected Sf9 cells or noninfected Sf9 cells, $Ni^{2+}$ affinity purified recombinant His-FKBP52-TP2, and nuclear extracts from Sf9 cells expressing recombinant FKBP46 or recombinant His-FKBP46 were fractionated on a 10% SDS-polyacrylamide gel, and transferred to nitrocellulose membrane. The membrane was incubated with a rabbit anti-FKBP46 polyclonal antibody and then detected by enhanced chemiluminescence. No FKBP46 band was observed in the cytosolic extracts. These data were also confirmed by indirect immunofluorescence, which showed mainly nuclear localization of FKBP46. The recombinant FKBP46 and His-FKBP46 were also detected by Western blot analysis and have the same electrophoretic mobility and nuclear localization as the endogenous FKBP46.

FKBP46 is a DNA Binding Protein—Sequence and structural analyses of the second basic domain of FKBP46 (FIG. 2B) suggest that FKBP46 might be a DNA binding protein. To test this possibility, we prepared recombinant FKBP46 and truncated FKBP46 lacking the entire FKBP-Hke domain and determined their ability to bind double-stranded DNA immobilized onto cellulose matrix. Western blot analysis of the DNA binding activity of FKBP46 was performed. Nuclear extract containing full-length FKBP46 and cytosolic extract containing truncated FKBP46 were bound to DNA cellulose and then analyzed. Full-length FKBP46 and truncated FKBP46 retained on DNA cellulose after elution with 0.6M NaCl, 0.3M NaCl, 0.15M NaCl, and 0.075M NaCl. Both full-length and truncated FKBP46 were able to bind DNA-cellulose at low salt concentration. High unit concentrations (300–600 mM NaCl) were required to elute both proteins from DNA-cellulose. These data suggest that FKBP46 has the ability to bind DNA and that this activity lies within its first N-terminal 312 amino acids. Therefore, The ability of FKBP46 to bind DNA is consistent with its nuclear localization and with the requirement of high salt concentrations to extract it from Sf9 nuclei.

Figure 3B:
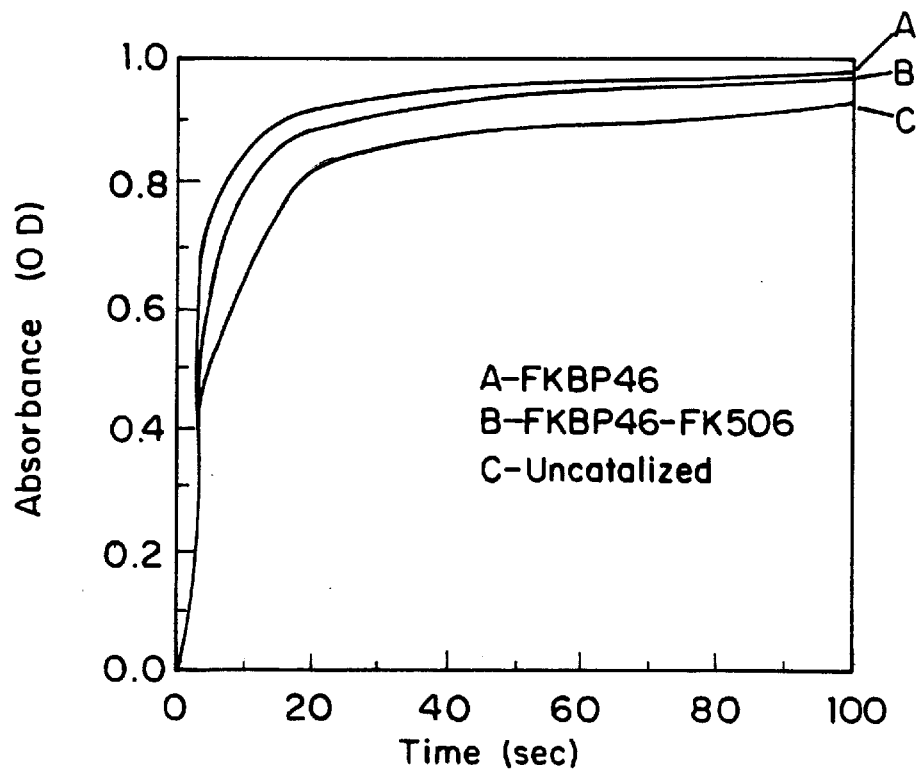

FKBP46 Can Bind FK506 and Possesses Peptidylprolyl cistrans Isomerase Activity—To test the ability of FKBP46 to bind FK506, different amounts of purified His-FKBP46 immobilized on $Ni^{2+}$ affinity resin were incubated with $[^3H]$dihydro-FK506 in the presence or absence of cold FK506. The radioactivity associated with FKBP46 was measured by scintillation counting. FIG. 3A shows that $[^3H]$dihydro-FK506 can bind specifically to FKBP46 in a dose-dependent manner. Under these conditions, maximal binding was obtained when 10 μl of nuclear extracts containing recombinant His-FKBP46 were immobilized on $Ni^{2+}$ affinity resin (FIG. 3A, column 6). No further increase in $[^3H]$dihydro-FK506 binding was observed with larger amounts of nuclear extracts. Mock purified wild type nuclear extract immobilized on $Ni^{2+}$ affinity resins showed minimal $[^3H]$dihydro-FK506 binding (FIG. 3A, column 1), which was comparable with binding values obtained with FKBP46 in the presence of excess cold FK506 (FIG. 3A, columns 3, 5, and 7). To determine the cis to trans isomerase activity of the recombinant FKBP46, purified His-FKBP46 was incubated with the peptide substrate N-succinyl-Ala-Leu-Pro-Phe-p-nitroanilide. Under equilibrium conditions, about 88% of the peptide is present as the trans form, and 12% is present as the cis form (Siekierka, J. J., et al. (1990) *J. Biol. Chem.* 265, 21011–21015 which is incorporated herein by reference). Chymotrypsin hydrolyzes the trans form to generate p-nitroanilide, which can be quantitated spectrophotometrically at 400 nm. As shown in FIG. 3B, when chymotrypsin is added to the uncatalyzed reaction that does not contain FKBP46 (curve C), an initial rapid increase in absorbance due to the hydrolysis of the trans peptide occurs within the first 10 s. The hydrolysis of the remaining cis peptide is rate-limited by its conversion to the trans form and follows a simple first-order rate law. In the presence of FKBP46 (curve A) an acceleration of the rate of conversion of the cis to the trans peptide is observed. This acceleration can be significantly inhibited by FK506 (curve B). From these curves, the specific activity of FKBP46 was calculated using the first order rate constant $(S^{-1})$, and the molar concentration of FKBP46 to be about $7.8 \times 10^6 \, s^{-1} \cdot M^{-1}$. This value is similar to the specific activity of hFKBP12, which is about $4.3 \times 10^6 \, s^{-1} \cdot M^{-1}$ (19). In the presence of FK506, we observed about 50% inhibition of FKBP46 activity (curve B).

A colinear alignment of the FKBP-like domain of FKBP46 with the FKBP-like domain of hFKBP12 (FIG. 2A) revealed that 11 of the 14 residues involved in the interaction of hFKBP12 and FK506 ($Tyr^{27}$, $Phe^{37}$, $Asp^{38}$, $Arg^{43}$, $Phe^{47}$, $Gln^{54}$, $Glu^{55}$, $Val^{56}$, $Ile^{57}$, $Trp^{60}$, $Tyr^{83}$, $His^{88}$, $Ile^{92}$, and $Phe^{100}$ in hFKBP12) (Van Duyne, G. D., et al. (1991) *Science* 252, 839–842 which is a incorporated herein by reference) are conserved in the FKBP-like domain of FKBP46. $Arg^{43}$, $Gln^{54}$, and $His^{88}$ of hFKBP12 are substituted in FKBP46 by Lys, Lys, and Ser, respectively. $Gln^{54}$ and $His^{88}$ of hFKBP12 also are not conserved in mFKBP52. The equivalent of $Phe^{37}$ and $Asp^{38}$ of hFKBP12 are frameshifted by 1 residue in FKBP46. This apparently does not affect the ability of FKBP46 to interact with FK506, nor does it affect its isomerase activity, but it may affect its substrate specificity. These observations suggest that the FKBP-like domain of FKBP46 is similar to hFKBP12 in both structure and function.

Association of FKBP46 with a Recombinant Mouse FKBP52-TP2 Fusion Protein—There are two cDNA clones for the mouse FKBP52 deposited in the GenBank under accession numbers X17068 and X17069 which are incorporated herein by reference. The X17068 codes for a fusion protein of FKBP52 and TP2 and the X17069 codes for a nonfusion FKBP52.

In vivo interaction of FKBP46 with His-FKBP52-TP2 fusion protein and with TP2 was analyzed. Sf9 cells were coinfected with recombinant baculoviruses AcNPV-FKBP46 and AcNPV-His-FKBP52-TP2. Nuclear extracts were prepared from these cells at 48 h postinfection and adsorbed to $Ni^{2+}$ resins, washed several times, eluted with Laemmli sample buffer, and then analyzed by SDS-PAGE (10% polyacrylamide gel) and Coomassie staining. In other experiments, nuclear extracts from Sf9 cells infected with either the wild type virus or recombinant GR, AcNPV-TP2 or AcNPV-His-FKBP52-TP2 baculoviruses were adsorbed to $Ni^{2+}$ resins. The resins were washed several times, incubated with $[\gamma\text{-}^{32}P]$ ATP and $Mg^{2+}$, and the proteins were then analyzed on a 12% SDS-polyacrylamide gel and visualized by Coomassie staining and autoradiography.

The resin can bind only the His-FKBP52-TP2 but not the recombinant FKBP46, which does not have a (His) 6 tag. However, when co-overexpressed in the same cell, a complex formation between the two proteins allows them to bind together to the affinity resin. Endogenous FKBP46 can associate with the His-FKBP52-TP2 in vivo. Because TP2 is a highly basic protein (Cole, K. D., and Kistler, W. S. (1987) *Biochem, Biophys. Res. Commun.* 147, 437–442 which is incorporated herein by reference) and FKBP46 contains two highly acidic domains, it appears that FKBP46 interacts with TP2 and not with FKBP52. To demonstrate this, TP2 was overexpressed in Sf9 cells. Nuclear extracts were prepared from cells infected with either wild type virus or recombinant GR, His-FKBP52-TP2, or TP2 baculoviruses and then adsorbed to $Ni^{2+}$ affinity resin. To assay for kinase activity associated with the adsorbed proteins, the resins were incubated with $[\gamma-^{32}P]ATP$ in the presence of $Mg^{2+}$ and then analyzed by SDS-PAGE and autoradiography. Coomassie staining of the resin-adsorbed proteins shows that TP2 can bind to $Ni^{2+}$ resin even without a $(His)_6$ tag because it has His domains and has been shown to be a zinc-binding protein (Baskaran, R., and Rao, M. R .S. (1991) *Biochem. Biophys. Res. Commun.* 179, 1491–1499 which is incorporated herein by reference). In addition, both TP2 and His-FKBP-52-TP2 preparations contain the FKBP46 band. The FKBP46 band is not present in the wild type or GR virus controls. Furthermore, the autoradiogram shows an FKBP46 radioactive band present in the TP2 and His-FKBP-52-TP2 preparations, but not in the wild type or GR preparations. These data suggest that FKBP46 is associated with TP2 and not with FKBP-52.

The FKBP-like Domain Influences the Nuclear Localization of the FKBP46—In vivo interaction of truncated FKBP46 with TP2 was studied. Sf9 cells were infected with AcNPV-His-tFKBP46 alone or coinfected with recombinant baculoviruses AcNPV-His-tFKBP46 and AcNPV-TP2. Cytosolic (cytosol) and nuclear (nuclei) extracts were prepared from these cells and then analyzed by SDS-PAGE and Coomassie staining. In the course of expression of a truncated FKBP46 that lacks the entire FKBP-like domain (amino acids 312–412), the truncated FKBP46 is expressed mainly in the cytosol of Sf9 cells. This suggests that the FKBP-like domain may contain the relevant nuclear localization signals or that its presence may be necessary for correct folding of the protein to translocate to the nucleus. Nuclear localization signal of the mammalian FKBP25 is present in its FKBP-like domain (Galat, A., et al. (1992) *Biochemistry* 31, 2427–2434 which is incorporated herein by reference). Overexpression of human FKBP25 (hFKBP25) in Sf9 cells resulted in nuclear localization. Overexpression of hFKBP52 in Sf9 cells resulted in cytoplasmic localization. The pI values of the FKBP-like domains of FKBP46, hFKBP25, hFKBP12, and hFKBP52 are 9.8, 9.39, 8.35 and 5.58, respectively. These data suggest that the FKBP-like domains of FKBP46 and hFKBP25 are more basic compared with those of hFKBP12 and hFKBP52. This implies that a correlation exists between the pI value of the FKBP-like domain and its subcellular localization. The more basic the FKBP-like domain is, the more likely it will be localized to the nucleus. After deletion of the C-terminal FKBP-like domain of FKBP46, the truncated protein has a highly acidic pI of 4.2. To test the possibility that the N-terminal acidic domains of FKBP46 are responsible for its interaction with nuclear basic proteins such as TP2, the truncated FKBP46 and TP2 were coexpressed in the same cell. Because TP2 is a nuclear DNA binding protein, interaction of TP2 with the truncated FKBP46 should result in nuclear localization of the truncated protein. Coexpression of the two proteins resulted in nuclear localization of both proteins. These observations suggest that interaction of TP2 with FKBP46 involves the acidic domains of FKBP46. The significance of this interaction lies in the ability of FKBP46 to interact with positively charged basic nuclear proteins such as TP2. Although TP2 is not normally expressed in Sf9 cells other nuclear chromatin proteins with similar charge to TP2 may interact with FKBP46. Such interactions may be important for nuclear functions.

FKBP46 Forms an FKBP-Kinase Complex—Incubation of TP2 or His-FKBP52-TP2 preparations with $[\gamma-^{32}P]ATP$ and $MgCl_2$ resulted in the phosphorylation of the associated FKBP46. To determine whether the recombinant FKBP46 can be phosphorylated in the absence of TP2 and FKBP52, recombinant His-FKBP46 was adsorbed to $Ni^{2+}$ resin, and aliquots of the resin were incubated with $[\gamma-^{32}P]ATP$ in the presence or absence of $Ca^{2+}$ or $Mg^{2+}$ and then analyzed by SDS-PAGE and autoradiography. Kinase activity associated with FKBP46 was analyzed. Nuclear extract from Sf9 cells expressing recombinant His-FKBP46 was adsorbed to $Ni^{2+}$ affinity resin and washed several times with a low salt washing buffer, and then aliquots of the resin were incubated with $[\gamma-^{32}P]ATP$ in the absence or presence of $Mg^{2+}$ (0.2 mM) or $Ca^{2+}$ (0.2 mM) and then analyzed by SDS-PAGE and autoradiography. Endogenous FKBP46 was immunoprecipitated from nuclear extract of noninfected Sf9 cells and then divided into three aliquots. One aliquot was washed twice with high salt buffer and the remaining two were washed twice with low salt buffer. All aliquots were then washed twice with low salt buffer and incubated in the same buffer in the presence of $Mg^{2+}$ and $[\gamma-^{32}P]ATP$ for 30 min. After the incubation, the samples were washed with low salt buffer or washed twice with high salt buffer and then analyzed by SDS-PAGE and autoradiography. The recombinant His-FKBP46 was highly phosphorylated only in the presence of $Mg^{2+}$. This result suggests that FKBP46 is a kinase that autophosphorylates itself or is a substrate for an associated kinase. A homology search of data bases with the amino acid sequence of FKBP46 did not reveal any kinase domains. Therefore, to test the second possibility, a nuclear extract from uninfected Sf9 nuclei was immunoprecipitated with a polygonal antibody raised against FKBP46. The immunoprecipitated endogenous FKBP46 was washed either with high salt or low salt buffers and then assayed for kinase activity. Phosphorylation of the high salt-washed FKBP46 was dramatically reduced compared with the low salt-washed or postkinase activity high salt-washed controls. Similar results were obtained with recombinant His-FKBP46 immobilized on $Ni^{2+}$ resin. These results suggest that FKBP46 is phosphorylated by an associated kinase that can be dissociated with high salt treatment. This kinase is a $Mg^{2+}$-dependent protein-kinase that specifically phosphorylates FKBP46. FKBP52 may not be a substrate for this kinase because only FKBP46 undergoes phosphorylation when the His-FKBP52-TP2/FKBP46 complex is incubated with $[\gamma-^{32}P]ATP$ and $Mg^{2+}$. This kinase might be the insect analog of casein kinase II or a similar kinase that associates with nuclear immunophilins. It has been shown that casein kinase II is associated with the mammalian nuclear FKBP25. The presence of FKBP-kinase complexes in the nucleus of mammalian and insect cells suggests that the function of these proteins is regulated by phosphorylation and might be conserved in evolution. In fact, several casein kinase II phosphorylation sites exist in the N-termini of both FKBP46 and FKBP25. Association of an FKBP with a kinase may otherwise regulate the function of the kinase itself. Through their activity as peptidylprolyl isomerases, nuclear FKBPs could maintain kinase function by properly folding the kinase complex, and this complex might play a role in nuclear signal transduction. Many nuclear proteins could also be substrates for nuclear immunophilins. Their isomerase activity may, for example, be required for proper folding and stability of certain short-lived labile transcription factors.

Example 2

Western blot analysis of Sf FKBP46: Sf9 cells were infected with wild type or vp35Δ, i.e. baculovirus which does not express viral protein 35, and harvested 24–46 h after infection. The cells were lysed and the cell lysates were centrifuged at 800 g for 15 min and the nuclear pellets were collected and then suspended in SDS-sample buffer. The nuclear proteins were fractionated by SDS-PAGE, electroblotted onto a PVDF membrane and detected by Western blotting using a rabbit polyclonal antibody raised against Sf9 FKBP46. In some experiments, Sf9 cells were infected with recombinant baculovirus encoding Sf Caspase-1 and their proteins were analyzed as described above.

The nuclear Sf FKBP46 is a target of Sf Caspase-1 in baculovirus-induced apoptosis. FKBP46 contains two N-terminal acidic domains with uninterrupted stretches of polyglutamic/aspartic acid residues. Because of the high content of Asp residues in these domains we decided to test whether FKBP46 is a target of Sf Caspase-1 in apoptosis. Sf9 cells were infected with wild type (WT) baculovirus (encodes p35) or p35 null mutant (vp35Δ) baculovirus and harvested 24 h after infection. Western blot analysis revealed that FKBP46 is cleaved to a ~25 kDa fragment in Sf9 cells infected with vp35Δ but not with wild type virus.

Data from experiments evaluating cleavage of the Sf nuclear immunophilin FKBP46 by Sf Caspase-1 and during vp35Δ baculovirus-induced apoptosis was generated. Purified recombinant Sf FKBP46 or nuclei from wild type virus infected Sf9 cells (24 h post-infection) were incubated with (+) or without (−) recombinant Sf Caspase-1 for 1 h at 37° C. and then analyzed by SDS-PAGE and immunoblotting with an FKBP46-specific polyclonal antibody. Nuclei from vp35Δ baculovirus-infected Sf9 cells (Δp35) were isolated and directly analyzed by SDS-PAGE and immunoblotting. Full length and 30 kDa cleavage product of FKBP46 are indicated.

Since cells infected with vp35Δ virus but not wild type virus undergo rapid apoptosis as a result of activation of Sf Caspase-1, it is most likely that Sf Caspase-1 is the enzyme responsible for cleaving FKBP46. This was supported by our observations that incubation of recombinant Sf Caspase-1 with purified recombinant FKBP46 or Sf9 nuclei yielded the same ~25 kDa cleavage product.

Data also shows that overexpression of Sf proCaspase-1 in SF9 cells results in its activation, cleavage of FKBP46 and DNA cleavage. Sf9 cells were infected with recombinant baculovirus encoding T7-tagged Sf proCaspase-1 under the polyhedrin promoter or wild type baculovirus. The activity in the Sf Caspase-1 virus lysates was expressed relative to the activity in the wild type virus lysate. Data from experiments evaluating induction of DNA cleavage by overexpressed Sf Caspase-1 was also generated using total DNA was isolated from Sf9 cells infected with wild type baculovirus (negative control) or recombinant baculoviruses encoding ProICEλ (positive control) or Sf proCaspase-1 and then analyzed by 1.8% agarose-gel electrophoresis. The data demonstrate that overexpression of Sf proCaspase-1 in Sf9 cells resulted in its processing as determined by immunostaining with T7 antibody and generation of maximal Sf Caspase-1 activity at 46 h post infection. The lower Sf Caspase-1 activity observed at 16–24 h post infection might be due to p35 inhibition which is stoichiometric. In addition, the lower T7-immunostaining observed at 46 h post infection is due to removal of the T7-tagged prodomain by the high Sf Caspase-1 activity. Maximal cleavage of FKBP46 and induction of apoptosis with characteristic internucleosomal DNA cleavage were observed at 46 h postinfection.

The death effector component is an ASCP named Sf-Caspase-1, highly related to the mammalian apoptotic effectors Mch3, CPP32 and Mch2α can cleave a death substrate known as FKBP46, which is an Sf9 nuclear DNA binding immunophilin. We demonstrated that FKBP46 is cleaved specifically during vp35Δ baculovirus-induced apoptosis of Sf9 cells and by the death effector component Sf Caspase-1.

We claim:

1. An isolated nucleic acid molecule that comprises a nucleic acid sequence that encodes the protein having the amino acid sequence of SEQ ID NO:2.

2. An isolated nucleic acid molecule consisting of SEQ ID NO:1 or a fragment thereof having at least 10 contiguous nucleotides of a unique nucleotide sequence of SEQ ID NO:1.

3. The nucleic acid molecule of claim 2 consisting of SEQ ID NO:1.

4. A recombinant expression vector comprising the nucleic acid molecule of claim 3.

5. A host cell comprising the recombinant expression vector of claim 4.

6. The nucleic acid molecule of claim 2 consisting of a fragment of SEQ ID NO:1 having at least 10 contiguous nucleotides of a unique nucleotide sequence of SEQ ID NO:1.

7. The nucleic acid molecule of claim 2 consisting of a fragment of SEQ ID NO:1 having at least 150 contiguous nucleotides of a unique nucleotide sequence of SEQ ID NO:1.

8. The nucleic acid molecule of claim 2 consisting of a fragment of SEQ ID NO:1 having 15–50 contiguous nucleotides of a unique nucleotide sequence of SEQ ID NO:1.

9. An oligonucleotide molecule comprising a nucleotide sequence complimentary to a nucleotide sequence of at least 10 contiguous nucleotides of a unique nucleotide sequence of SEQ ID NO:1.

10. The oligonucleotide molecule of claim 9 wherein said oligonucleotide molecule comprises a nucleotide sequence complimentary to a nucleotide sequence of at least 16 contiguous nucleotides of a unique nucleotide sequence of SEQ ID NO:1.

11. The oligonucleotide molecule of claim 9 wherein said oligonucleotide molecule comprises a nucleotide sequence complimentary to a nucleotide sequence of at least 24 contiguous nucleotides of a unique nucleotide sequence of SEQ ID NO:1.

12. The oligonucleotide molecule of claim 9 consisting of a nucleotide sequence complimentary to a nucleotide sequence of at least 150 contiguous nucleotides of a unique nucleotide sequence of SEQ ID NO:1.

13. The oligonucleotide molecule of claim 9 consisting of a nucleotide sequence complimentary to a nucleotide sequence of 18–28 contiguous nucleotides of a unique nucleotide sequence of SEQ ID NO:1.

14. A recombinant expression vector comprising the nucleic acid molecule of claim 1.

15. A host cell comprising the recombinant expression vector of claim 14.

16. An isolated nucleic acid molecule consisting of SEQ ID NO:1 or a fragment thereof having at least 24 contiguous nucleotides of SEQ ID NO:1.

17. The nucleic acid molecule of claim 16 consisting of a fragment of SEQ ID NO:1 having at least 24 contiguous nucleotides of SEQ ID NO:1.

18. An oligonucleotide molecule comprising a nucleotide sequence of at least 24 contiguous nucleotides of SEQ ID NO:1.

19. The oligonucleotide molecule of claim 18 consisting of a nucleotide sequence complimentary to a nucleotide sequence of up to 150 contiguous nucleotides of SEQ ID NO:1.

20. An isolated nucleic acid molecule consisting of SEQ ID NO:1 or a fragment thereof having at least 10 contiguous nucleotides of a nucleotide sequence selected from the group consisting of: nucleotides 100–429 of SEQ ID NO:1, nucleotides 442–462 of SEQ ID NO:1, nucleotides 472–501 of SEQ ID NO:1, nucleotides 514–540 of SEQ ID NO:1, nucleotides 547–741 of SEQ ID NO:1, nucleotides 769–846 of SEQ ID NO:1, nucleotides 868–912 of SEQ ID NO:1, nucleotides 925–948 of SEQ ID NO:1, nucleotides 958–972 of SEQ ID NO:1, nucleotides 1006–1335 of SEQ ID NO:1.

21. The nucleic acid molecule of claim 20 consisting of SEQ ID NO:1 or a fragment thereof having at least 16 contiguous nucleotides of a nucleotide sequence selected from the group consisting of: nucleotides 100–429 of SEQ ID NO:1, nucleotides 442–462 of SEQ ID NO:1, nucleotides 472–501 of SEQ ID NO:1, nucleotides 514–540 of SEQ ID NO:1, nucleotides 547–741 of SEQ ID NO:1, nucleotides 769–846 of SEQ ID NO:1, nucleotides 868–912 of SEQ ID NO:1, nucleotides 925–948 of SEQ ID NO:1, nucleotides 1006–1335 of SEQ ID NO:1.

22. The nucleic acid molecule of claim 20 consisting of SEQ ID NO:1 or a fragment thereof having at least 24 contiguous nucleotides of a nucleotide sequence selected from the group consisting of: nucleotides 100–429 of SEQ ID NO:1, nucleotides 472–501 of SEQ ID NO:1, nucleotides 514–540 of SEQ ID NO:1, nucleotides 547–741 of SEQ ID NO:1, nucleotides 769–846 of SEQ ID NO:1, nucleotides 868–912 of SEQ ID NO:1, nucleotides 1006–1335 of SEQ ID NO:1.

23. An oligonucleotide molecule comprising a nucleotide sequence complimentary to a nucleotide sequence of at least at least 10 contiguous nucleotides of a nucleotide sequence selected from the group consisting of: nucleotides 100–429 of SEQ ID NO:1, nucleotides 442–462 of SEQ ID NO:1, nucleotides 472–501 of SEQ ID NO:1, nucleotides 514–540 of SEQ ID NO:1, nucleotides 547–741 of SEQ ID NO:1, nucleotides 769–846 of SEQ ID NO:1, nucleotides 868–912 of SEQ ID NO:1, nucleotides 925–948 of SEQ ID NO:1, nucleotides 958–972 of SEQ ID NO:1, nucleotides 1006–1335 of SEQ ID NO:1.

24. The oligonucleotide molecule of claim 23 wherein said oligonucleotide molecule comprises a nucleotide sequence complimentary to a nucleotide sequence of at least at least 16 contiguous nucleotides of a nucleotide sequence selected from the group consisting of: nucleotides 100–429 of SEQ ID NO:1, nucleotides 442–462 of SEQ ID NO:1, nucleotides 472–501 of SEQ ID NO:1, nucleotides 514–540 of SEQ ID NO:1, nucleotides 547–741 of SEQ ID NO:1, nucleotides 769–846 of SEQ ID NO:1, nucleotides 868–912 of SEQ ID NO:1, nucleotides 925–948 of SEQ ID NO:1, nucleotides 1006–1335 of SEQ ID NO:1.

25. The oligonucleotide molecule of claim 23 wherein said oligonucleotide molecule comprises a nucleotide sequence complimentary to a nucleotide sequence of at least at least 24 contiguous nucleotides of a nucleotide sequence selected from the group consisting of: nucleotides 100–429 of SEQ ID NO:1, nucleotides 472–501 of SEQ ID NO:1, nucleotides 514–540 of SEQ ID NO:1, nucleotides 547–741 of SEQ ID NO:1, nucleotides 769–846 of SEQ ID NO:1, nucleotides 868–912 of SEQ ID NO:1, nucleotides 1006–1335 of SEQ ID NO:1.

* * * * *

UNITED STATES PATENT AND TRADEMARK OFFICE
CERTIFICATE OF CORRECTION

PATENT NO. : 5,861,498
DATED : January 19, 1999
INVENTOR(S) : Emad S. Alnemri et al It is certified that error appears in the above-identified patent and that said Letters Patent is hereby corrected as shown below:

Col. 15, line 2, (His)6 should be --(His)$_6$--

Signed and Sealed this

Fourteenth Day of September, 1999

Attest:

Q. TODD DICKINSON

*Attesting Officer*      *Acting Commissioner of Patents and Trademarks*

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 2255 base pairs
        ( B ) TYPE: nucleic acid
        ( C ) STRANDEDNESS: double
        ( D ) TOPOLOGY: Not Relevant ( i i ) MOLECULE TYPE: cDNA ( i x ) FEATURE:
        ( A ) NAME/KEY: CDS
        ( B ) LOCATION: 160..1398

( x i ) SEQUENCE DESCRIPTION: SEQ ID NO:1:

```
GAATTCGGCA   CGAGCTTGAT   TTTGCCGCGT   TTGAACGCAT   GCTGTGATCC   ACATTTGAAT        60
```

```
AAAGAAACC  GGCAAAACTA  TTTTATTATT  TAGTGTCGTA  ATAAACTTTC  TTTTAAAGCC                                          120

GAATTATATC  TATAGTTTGT  TATAAATAAA  AACGTCAAA  ATG TTT TGG GGA CTT                                             174
                                               Met Phe Trp Gly Leu
                                                1           5

ATT ATG GAA CCG AAC AAA CGG TAC ACC CAA GTG GTG GAG AAA CCG TTC                                               222
Ile Met Glu Pro Asn Lys Arg Tyr Thr Gln Val Val Glu Lys Pro Phe
            10                  15                  20

CAC ATC TCA CAG GCA GCT ATG GAC ATC AGC ACC GGA GAC AAT GAT CCC                                               270
His Ile Ser Gln Ala Ala Met Asp Ile Ser Thr Gly Asp Asn Asp Pro
                25              30                  35

TGC CAA GTT ATG GTA GTA GTC GAT GGC AAG AAC TTC CTA GTG TGC ACA                                               318
Cys Gln Val Met Val Val Val Asp Gly Lys Asn Phe Leu Val Cys Thr
        40              45                  50

TTA CAG AAG GGC AAG ATT ATC CAG GTG CCC TTG GAC TTG TAT TTC AAA                                               366
Leu Gln Lys Gly Lys Ile Ile Gln Val Pro Leu Asp Leu Tyr Phe Lys
    55              60                  65

TCT GGA GAT TCA GTT TCA TTC TTG ACA AAT GGT AAA TGC AAT GTT CAC                                               414
Ser Gly Asp Ser Val Ser Phe Leu Thr Asn Gly Lys Cys Asn Val His
70              75                  80                      85

TTG ACT GGT TAC CTT GAT CCT GAG TTT GAG GAG GAT TTG GAG GAT GAG                                               462
Leu Thr Gly Tyr Leu Asp Pro Glu Phe Glu Glu Asp Leu Glu Asp Glu
            90                  95                  100

GAA GAG GCT GAA GAA GAA GAG GAG GAG GAG GCT CCA CCT CTA GTG                                                   510
Glu Glu Ala Glu Glu Glu Glu Glu Glu Glu Ala Pro Pro Leu Val
                105                 110                 115

CCA GCT AAG AAT AAG AGG AAA CTC GAG AAT GCC AAT GAT GCC ACA GCT                                               558
Pro Ala Lys Asn Lys Arg Lys Leu Glu Asn Ala Asn Asp Ala Thr Ala
        120                 125                 130

AAC AAA AAG GCC AAG CCT GAC AAG AAA GCT GGC AAG AAC AGT GCA CCA                                               606
Asn Lys Lys Ala Lys Pro Asp Lys Lys Ala Gly Lys Asn Ser Ala Pro
135                 140                 145

GCA GCA GAA AGT GAT TCA GAT GAC GAT GAT GAA GAC CAG CTT CAA AAG                                               654
Ala Ala Glu Ser Asp Ser Asp Asp Asp Asp Glu Asp Gln Leu Gln Lys
150                 155                 160                 165

TTC CTT GAC GGT GAA GAT ATA GAC ACT GAT GAA AAT GAT GAA TCA TTC                                               702
Phe Leu Asp Gly Glu Asp Ile Asp Thr Asp Glu Asn Asp Glu Ser Phe
            170                 175                 180

AAA ATG AAC ACA TCA GCT GAA GGA GAT GAC AGT GAT GAA GAG GAT GAT                                               750
Lys Met Asn Thr Ser Ala Glu Gly Asp Asp Ser Asp Glu Glu Asp Asp
            185                 190                 195

GAT GAA GAC GAA GAG GAT GAA GAA GAT GAT GAT GAG GAC GAT GAA GAA                                               798
Asp Glu Asp Glu Glu Asp Glu Glu Asp Asp Asp Glu Asp Asp Glu Glu
            200                 205                 210

GAG GAG GAA GCA CCC AAG AAG AAG AAA CAG CCA GCC GCA GAG CAG                                                   846
Glu Glu Glu Ala Pro Lys Lys Lys Lys Gln Pro Ala Ala Glu Gln
    215                 220                 225

GAC TCA ACA CTG GAC ACA AGC AAG GAG TCT GTG GAC ATG TCC AAA CTG                                               894
Asp Ser Thr Leu Asp Thr Ser Lys Glu Ser Val Asp Met Ser Lys Leu
230                 235                 240                 245

TCC AAG TCA CAG AAG AGA AGG CTC AAG AAG AAG CTC CAA CAA CAA GCT                                               942
Ser Lys Ser Gln Lys Arg Arg Leu Lys Lys Lys Leu Gln Gln Gln Ala
            250                 255                 260

AAA CAA CAG CCT CAA GTC AAT GGA GTT GAT AAG CCT AAG AAA GAG GAA                                               990
Lys Gln Gln Pro Gln Val Asn Gly Val Asp Lys Pro Lys Lys Glu Glu
            265                 270                 275

CCC CAA CAG AAG GCT GAA AAG AAG AAG CCT GAG GCC AAG AAA GAA GAG                                              1038
Pro Gln Gln Lys Ala Glu Lys Lys Lys Pro Glu Ala Lys Lys Glu Glu
            280                 285                 290

GCT CCA GTA GAG AAG AAA GAA AAG AAA CAA ATT GCT GGT GGT GTT TCT                                              1086
```

```
              Ala  Pro  Val  Glu  Lys  Lys  Glu  Lys  Lys  Gln  Ile  Ala  Gly  Gly  Val  Ser
                   295                 300                      305

ATT  GAA  GAC  CTC  AAG  GTC  GGT  TCT  GGA  CCT  GTT  GCC  AAG  GCT  GGC  AAA                    1 1 3 4
Ile  Glu  Asp  Leu  Lys  Val  Gly  Ser  Gly  Pro  Val  Ala  Lys  Ala  Gly  Lys
310                 315                      320                      325

GTT  GTA  ATG  GTT  TAC  TAC  GAA  GGT  CGC  CTT  AAG  CAA  AAC  AAC  AAG  ATG                    1 1 8 2
Val  Val  Met  Val  Tyr  Tyr  Glu  Gly  Arg  Leu  Lys  Gln  Asn  Asn  Lys  Met
                    330                      335                      340

TTT  GAC  AAC  TGT  GTG  AAA  GGA  CCT  GGC  TTC  AAG  TTC  CGC  CTA  GGA  TCC                    1 2 3 0
Phe  Asp  Asn  Cys  Val  Lys  Gly  Pro  Gly  Phe  Lys  Phe  Arg  Leu  Gly  Ser
               345                      350                      355

AAG  GAG  GTC  ATC  TCT  GGC  TGG  GAT  GTA  GGT  ATT  GCT  GGC  ATG  AAG  GTT                    1 2 7 8
Lys  Glu  Val  Ile  Ser  Gly  Trp  Asp  Val  Gly  Ile  Ala  Gly  Met  Lys  Val
          360                      365                      370

GGA  GGC  AAG  AGG  AAG  ATC  GTC  TGC  CCA  CCT  GCA  ATG  GCG  TAT  GGA  GCC                    1 3 2 6
Gly  Gly  Lys  Arg  Lys  Ile  Val  Cys  Pro  Pro  Ala  Met  Ala  Tyr  Gly  Ala
     375                      380                      385

AAA  GGA  TCA  CCT  CCA  GTC  ATC  CCA  CCA  AAC  TCA  ACT  CTA  GTA  TTT  GAA                    1 3 7 4
Lys  Gly  Ser  Pro  Pro  Val  Ile  Pro  Pro  Asn  Ser  Thr  Leu  Val  Phe  Glu
390                 395                      400                      405

GTT  GAC  CTG  AAG  AAT  GTG  AAA  TAA  GTGAAATGTT  GATGAATGTG  CCAGTATGTC                         1 4 2 8
Val  Asp  Leu  Lys  Asn  Val  Lys   *
               410

GAGAACTTGT  TGATTTGCTT  TAATTGAATG  TTTATTGAAA  GGTTGACATT  GAATGCATGA                              1 4 8 8

TTGTTGAAAC  AGTTACAATG  TGCTCTATCT  GCAATAAGTT  TATTTTGTGT  GAATTAGAAG                              1 5 4 8

AGGTGCTACA  TATTGTGTAA  CATTATGATA  CTATTTCTTC  AATCATATCT  TGTTTTTCAT                              1 6 0 8

ATGAAAAATA  TCTTTATTCT  GAAATTACAT  AATTGTTTTT  CTATTGAACA  TCAGTAAAAT                              1 6 6 8

ATTGCAGGTA  TACCACATTG  TTGTCTACAG  CATAAGTTGT  CTTAAGTTAG  TTCATAAGGA                              1 7 2 8

TTTTACTGGA  CATGATAACT  TAAATTCAGC  TGCAGAATAA  ACCAAATTGT  TCTAAAAAAA                              1 7 8 8

TTTTGGTTTC  TGAAAAATAT  CCTGTCACTT  TTACCCAAAT  TCTATTTCCG  ATAAAATATT                              1 8 4 8

AAATAAATGT  TTTTTTTTA   ATAAAGTACC  AATAGAATGA  AGCCTCTGAT  GTAAATGTGT                              1 9 0 8

GACATCTATT  TCTGGTTAAG  ATAGTTATTA  ATTCCGACTA  TTATTATATA  AGGTTATTTT                              1 9 6 8

ACTAAGAAGT  TTTTCATGGA  AGACTTTCCA  TAGTAAACCA  GTATGCATTA  TACATGTAAG                              2 0 2 8

AGTAAAAGAT  ATGTTTGAAT  TTTAATAAAA  AACTAGACAA  TCATTCAGAG  CATGGACTAA                              2 0 8 8

TTTAAATTAT  TAGTTCATGA  TGCAGAGTAA  CACTCAACAA  TGATTATCTA  GTTTTGGGAC                              2 1 4 8

AAGCATAGTG  TACTACTCTT  TGTCATCTGC  ATGTATTCCA  CAAACTGTTG  GTATGACTAA                              2 2 0 8

GGTACTCTAA  TCAACCAAAA  TATTGTGAAA  TAAAAGTCAA  GAAGTCT                                             2 2 5 5
```

( 2 ) INFORMATION FOR SEQ ID NO:2:

( i ) SEQUENCE CHARACTERISTICS:
        ( A ) LENGTH: 412 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Phe  Trp  Gly  Leu  Ile  Met  Glu  Pro  Asn  Lys  Arg  Tyr  Thr  Gln  Val
 1              5                        10                      15

Val  Glu  Lys  Pro  Phe  His  Ile  Ser  Gln  Ala  Ala  Met  Asp  Ile  Ser  Thr
               20                  25                      30

Gly  Asp  Asn  Asp  Pro  Cys  Gln  Val  Met  Val  Val  Asp  Gly  Lys  Asn
          35                  40                      45
```

| | | | | | | | | | | | | | |
|---|---|---|---|---|---|---|---|---|---|---|---|---|---|
| Phe | Leu | Val | Cys | Thr | Leu | Gln | Lys | Gly | Lys | Ile | Ile | Gln | Val | Pro | Leu |
| | 50 | | | | | 55 | | | | | 60 | | | | |
| Asp | Leu | Tyr | Phe | Lys | Ser | Gly | Asp | Ser | Val | Ser | Phe | Leu | Thr | Asn | Gly |
| 65 | | | | | 70 | | | | | 75 | | | | | 80 |
| Lys | Cys | Asn | Val | His | Leu | Thr | Gly | Tyr | Leu | Asp | Pro | Glu | Phe | Glu |
| | | | | 85 | | | | | 90 | | | | | 95 |
| Asp | Leu | Glu | Asp | Glu | Glu | Glu | Ala | Glu | Glu | Glu | Glu | Glu | Glu | Glu |
| | | | 100 | | | | | 105 | | | | | 110 | |
| Ala | Pro | Pro | Leu | Val | Pro | Ala | Lys | Asn | Lys | Arg | Lys | Leu | Glu | Asn | Ala |
| | | 115 | | | | | 120 | | | | | 125 | | | |
| Asn | Asp | Ala | Thr | Ala | Asn | Lys | Lys | Ala | Lys | Pro | Asp | Lys | Lys | Ala | Gly |
| | 130 | | | | | 135 | | | | | 140 | | | | |
| Lys | Asn | Ser | Ala | Pro | Ala | Ala | Glu | Ser | Asp | Ser | Asp | Asp | Asp | Glu |
| 145 | | | | | 150 | | | | | 155 | | | | | 160 |
| Asp | Gln | Leu | Gln | Lys | Phe | Leu | Asp | Gly | Glu | Asp | Ile | Asp | Thr | Asp | Glu |
| | | | | 165 | | | | | 170 | | | | | 175 | |
| Asn | Asp | Glu | Ser | Phe | Lys | Met | Asn | Thr | Ser | Ala | Glu | Gly | Asp | Asp | Ser |
| | | | 180 | | | | | 185 | | | | | 190 | | |
| Asp | Glu | Glu | Asp | Asp | Asp | Glu | Glu | Glu | Asp | Glu | Glu | Asp | Asp | Asp |
| | | 195 | | | | | 200 | | | | | 205 | | | |
| Glu | Asp | Asp | Glu | Glu | Glu | Glu | Glu | Ala | Pro | Lys | Lys | Lys | Lys | Gln |
| 210 | | | | | | 215 | | | | | 220 | | | | |
| Pro | Ala | Ala | Glu | Gln | Asp | Ser | Thr | Leu | Asp | Thr | Ser | Lys | Glu | Ser | Val |
| 225 | | | | | 230 | | | | | 235 | | | | | 240 |
| Asp | Met | Ser | Lys | Leu | Ser | Lys | Ser | Gln | Lys | Arg | Arg | Leu | Lys | Lys | Lys |
| | | | | 245 | | | | | 250 | | | | | 255 | |
| Leu | Gln | Gln | Gln | Ala | Lys | Gln | Gln | Pro | Gln | Val | Asn | Gly | Val | Asp | Lys |
| | | | 260 | | | | | 265 | | | | | 270 | | |
| Pro | Lys | Lys | Glu | Glu | Pro | Gln | Gln | Lys | Ala | Glu | Lys | Lys | Pro | Glu |
| | 275 | | | | | 280 | | | | | 285 | | | | |
| Ala | Lys | Lys | Glu | Glu | Ala | Pro | Val | Glu | Lys | Lys | Glu | Lys | Lys | Gln | Ile |
| | 290 | | | | 295 | | | | | 300 | | | | | |
| Ala | Gly | Gly | Val | Ser | Ile | Glu | Asp | Leu | Lys | Val | Gly | Ser | Gly | Pro | Val |
| 305 | | | | | 310 | | | | | 315 | | | | | 320 |
| Ala | Lys | Ala | Gly | Lys | Val | Val | Met | Val | Tyr | Tyr | Glu | Gly | Arg | Leu | Lys |
| | | | | 325 | | | | | 330 | | | | | 335 | |
| Gln | Asn | Asn | Lys | Met | Phe | Asp | Asn | Cys | Val | Lys | Gly | Pro | Gly | Phe | Lys |
| | | | 340 | | | | | 345 | | | | | 350 | | |
| Phe | Arg | Leu | Gly | Ser | Lys | Glu | Val | Ile | Ser | Gly | Trp | Asp | Val | Gly | Ile |
| | | 355 | | | | | 360 | | | | | 365 | | | |
| Ala | Gly | Met | Lys | Val | Gly | Gly | Lys | Arg | Lys | Ile | Val | Cys | Pro | Pro | Ala |
| | | 370 | | | | 375 | | | | | 380 | | | | |
| Met | Ala | Tyr | Gly | Ala | Lys | Gly | Ser | Pro | Pro | Val | Ile | Pro | Pro | Asn | Ser |
| 385 | | | | | 390 | | | | | 395 | | | | | 400 |
| Thr | Leu | Val | Phe | Glu | Val | Asp | Leu | Lys | Asn | Val | Lys |
| | | | | 405 | | | | | 410 | | |

(2) INFORMATION FOR SEQ ID NO:3:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer"

5,861,498

-continued (x i) SEQUENCE DESCRIPTION: SEQ ID NO:3:

CCGGAATTCT GTTTTGGGGA CTTATTATGG                                                              30

(2) INFORMATION FOR SEQ ID NO:4:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "PCR primer"

(x i) SEQUENCE DESCRIPTION: SEQ ID NO:4:

CAGAACCGAC CTTGAGGTCT TA                                                                      22

(2) INFORMATION FOR SEQ ID NO:5:

(i) SEQUENCE CHARACTERISTICS:
        (A) LENGTH: 1236 base pairs
        (B) TYPE: nucleic acid
        (C) STRANDEDNESS: double
        (D) TOPOLOGY: Not Relevant (i i) MOLECULE TYPE: cDNA (i x) FEATURE:
        (A) NAME/KEY: CDS
        (B) LOCATION: 1..1236

(x i) SEQUENCE DESCRIPTION: SEQ ID NO:5:

```
ATG TCT GAT TTG TTA CCA CTA GCT ACC TAC AGT TTG AAT GTT GAA CCT        48
Met Ser Asp Leu Leu Pro Leu Ala Thr Tyr Ser Leu Asn Val Glu Pro
415             420                 425

TAT ACC CCG GTT CCA GCA ATC GAC GTC ACG ATG CCC ATC ACC GTT CGT        96
Tyr Thr Pro Val Pro Ala Ile Asp Val Thr Met Pro Ile Thr Val Arg
430             435                 440                 445

ATT ACT ATG GCT GCT TTG AAC CCG GAA GCC ATC GAT GAA GAG AAC AAA       144
Ile Thr Met Ala Ala Leu Asn Pro Glu Ala Ile Asp Glu Glu Asn Lys
                450                 455                 460

CCA TCG ACT TTA AGA ATT ATC AAA AGA AAC CCG GAC TTT GAA GAT GAT       192
Pro Ser Thr Leu Arg Ile Ile Lys Arg Asn Pro Asp Phe Glu Asp Asp
            465                 470                 475

GAT TTT TTA GGT GGT GAT TTT GAT GAA GAC GAA ATA GAC GAA GAA TCC       240
Asp Phe Leu Gly Gly Asp Phe Asp Glu Asp Glu Ile Asp Glu Glu Ser
            480                 485                 490

TCT GAG GAA GAA GAA GAG GAA AAA ACC CAA AAG AAA AAG AAG AGT AAA       288
Ser Glu Glu Glu Glu Glu Glu Lys Thr Gln Lys Lys Lys Lys Ser Lys
    495                 500                 505

GGC AAG AAG GCT GAA AGT GAA AGT GAG GAT GAT GAA GAA GAC GAT GAC       336
Gly Lys Lys Ala Glu Ser Glu Ser Glu Asp Asp Glu Glu Asp Asp Asp
510                 515                 520                 525

GAG GAC GAT GAG TTC CAA GAA TCC GTC CTT TTG ACT TTA TCT CCG GAA       384
Glu Asp Asp Glu Phe Gln Glu Ser Val Leu Leu Thr Leu Ser Pro Glu
                530                 535                 540

GCC CAA TAC CAA CAA TCT TTG GAC TTG ACC ATT ACT CCA GAA GAA GAA       432
Ala Gln Tyr Gln Gln Ser Leu Asp Leu Thr Ile Thr Pro Glu Glu Glu
            545                 550                 555

GTC CAA TTC ATT GTC ACT GGT TCT TAC GCT ATC TCC TTG AGC GGT AAC       480
Val Gln Phe Ile Val Thr Gly Ser Tyr Ala Ile Ser Leu Ser Gly Asn
            560                 565                 570

TAT GTT AAG CAT CCA TTT GAT ACT CCA ATG GGA GTC GAA GGT GAA GAC       528
Tyr Val Lys His Pro Phe Asp Thr Pro Met Gly Val Glu Gly Glu Asp
```

```
                        575                          580                          585
GAA  GAT  GAA  GAC  GCT  GAC  ATC  TAT  GAC  AGT  GAA  GAC  TAC  GAC  TTG  ACC        576
Glu  Asp  Glu  Asp  Ala  Asp  Ile  Tyr  Asp  Ser  Glu  Asp  Tyr  Asp  Leu  Thr
590                      595                      600                      605

CCA  GAT  GAG  GAT  GAA  ATT  ATT  GGC  GAC  GAC  ATG  GAC  GAC  TTG  GAT  GAC        624
Pro  Asp  Glu  Asp  Glu  Ile  Ile  Gly  Asp  Asp  Met  Asp  Asp  Leu  Asp  Asp
                         610                      615                      620

GAA  GAG  GAA  GAA  GAA  GTT  CGT  ATT  GAA  GAA  GTC  CAA  GAA  GAA  GAT  GAA        672
Glu  Glu  Glu  Glu  Glu  Val  Arg  Ile  Glu  Glu  Val  Gln  Glu  Glu  Asp  Glu
               625                      630                          635

GAA  GAT  AAT  GAT  GGA  GAA  GAA  GAA  CAA  GAA  GAA  GAA  GAA  GAA  GAA  GAA        720
Glu  Asp  Asn  Asp  Gly  Glu  Glu  Glu  Gln  Glu  Glu  Glu  Glu  Glu  Glu  Glu
          640                      645                      650

CAA  AAA  GAA  GAA  GTT  AAG  CCA  GAA  CCT  AAG  AAA  AGC  AAA  AAG  GAA  AAA        768
Gln  Lys  Glu  Glu  Val  Lys  Pro  Glu  Pro  Lys  Lys  Ser  Lys  Lys  Glu  Lys
     655                      660                      665

AAG  AGA  AAG  CAC  GAA  GAG  AAA  GAA  GAA  GAA  AAG  AAA  GCT  AAA  AAA  GTA        816
Lys  Arg  Lys  His  Glu  Glu  Lys  Glu  Glu  Glu  Lys  Lys  Ala  Lys  Lys  Val
670                      675                      680                      685

AAG  AAG  GTC  GAA  TTC  AAG  AAG  GAC  TTA  GAG  GAG  GGT  CCA  ACA  AAA  CCC        864
Lys  Lys  Val  Glu  Phe  Lys  Lys  Asp  Leu  Glu  Glu  Gly  Pro  Thr  Lys  Pro
                    690                      695                      700

AAA  AGC  AAA  AAG  GAA  CAA  GAT  AAG  CAT  AAA  CCA  AAG  AGT  AAG  GTT  TTG        912
Lys  Ser  Lys  Lys  Glu  Gln  Asp  Lys  His  Lys  Pro  Lys  Ser  Lys  Val  Leu
          705                      710                      715

GAA  GGC  GGC  ATA  GTA  ATC  GAA  GAC  CGT  ACT  ATC  GGT  GAT  GGC  CCA  CAG        960
Glu  Gly  Gly  Ile  Val  Ile  Glu  Asp  Arg  Thr  Ile  Gly  Asp  Gly  Pro  Gln
               720                      725                      730

GCT  AAG  AGA  GGT  GCC  AGA  GTA  GGC  ATG  AGG  TAC  ATT  GGT  AAG  TTA  AAG       1008
Ala  Lys  Arg  Gly  Ala  Arg  Val  Gly  Met  Arg  Tyr  Ile  Gly  Lys  Leu  Lys
     735                      740                      745

AAC  GGT  AAA  GTT  TTC  GAC  AAG  AAC  ACC  AGC  GGT  AAA  CCA  TTT  GCA  TTC       1056
Asn  Gly  Lys  Val  Phe  Asp  Lys  Asn  Thr  Ser  Gly  Lys  Pro  Phe  Ala  Phe
750                      755                      760                      765

AAA  CTT  GGC  CGT  GGT  GAA  GTT  ATC  AAA  GGC  TGG  GAC  ATT  GGT  GTT  GCC       1104
Lys  Leu  Gly  Arg  Gly  Glu  Val  Ile  Lys  Gly  Trp  Asp  Ile  Gly  Val  Ala
                    770                      775                      780

GGT  ATG  TCT  GTT  GGT  GGC  GAA  CGT  AGA  ATC  ATC  ATT  CCA  GCA  CCA  TAT       1152
Gly  Met  Ser  Val  Gly  Gly  Glu  Arg  Arg  Ile  Ile  Ile  Pro  Ala  Pro  Tyr
               785                      790                      795

GCC  TAC  GGG  AAG  CAA  GCT  CTG  CCA  GGT  ATT  CCT  GCC  AAT  TCC  GAA  CTG       1200
Ala  Tyr  Gly  Lys  Gln  Ala  Leu  Pro  Gly  Ile  Pro  Ala  Asn  Ser  Glu  Leu
          800                      805                      810

ACA  TTC  GAC  GTT  AAA  TTG  GTT  TCT  ATG  AAA  AAC  TAG                           1236
Thr  Phe  Asp  Val  Lys  Leu  Val  Ser  Met  Lys  Asn   *
815                      820                      825
```

(2) INFORMATION FOR SEQ ID NO:6:

(i) SEQUENCE CHARACTERISTICS:
        (A) LENGTH: 411 amino acids
        (B) TYPE: amino acid
        (D) TOPOLOGY: linear (ii) MOLECULE TYPE: protein (xi) SEQUENCE DESCRIPTION: SEQ ID NO:6:

```
Met  Ser  Asp  Leu  Leu  Pro  Leu  Ala  Thr  Tyr  Ser  Leu  Asn  Val  Glu  Pro
 1              5                        10                       15

Tyr  Thr  Pro  Val  Pro  Ala  Ile  Asp  Val  Thr  Met  Pro  Ile  Thr  Val  Arg
               20                        25                       30
```

| | | | | | | | | | | | | | | |
|---|---|---|---|---|---|---|---|---|---|---|---|---|---|---|
|Ile|Thr|Met|Ala|Ala|Leu|Asn|Pro|Glu|Ala|Ile|Asp|Glu|Asn|Lys|
| | |35| | | | |40| | | |45| | | |
|Pro|Ser|Thr|Leu|Arg|Ile|Ile|Lys|Arg|Asn|Pro|Asp|Phe|Glu|Asp|Asp|
| |50| | | | |55| | | |60| | | | |
|Asp|Phe|Leu|Gly|Gly|Asp|Phe|Asp|Glu|Asp|Glu|Ile|Asp|Glu|Glu|Ser|
|65| | | | |70| | | |75| | | | | |80|
|Ser|Glu|Glu|Glu|Glu|Glu|Glu|Lys|Thr|Gln|Lys|Lys|Lys|Lys|Ser|Lys|
| | | | |85| | | |90| | | | |95| |
|Gly|Lys|Lys|Ala|Glu|Ser|Glu|Ser|Glu|Asp|Asp|Glu|Glu|Asp|Asp|Asp|
| | | |100| | | |105| | | | |110| | |
|Glu|Asp|Asp|Glu|Phe|Gln|Glu|Ser|Val|Leu|Leu|Thr|Leu|Ser|Pro|Glu|
| | |115| | | |120| | | | |125| | | |
|Ala|Gln|Tyr|Gln|Gln|Ser|Leu|Asp|Leu|Thr|Ile|Thr|Pro|Glu|Glu|Glu|
| |130| | | |135| | | | |140| | | | |
|Val|Gln|Phe|Ile|Val|Thr|Gly|Ser|Tyr|Ala|Ile|Ser|Leu|Ser|Gly|Asn|
|145| | | |150| | | | |155| | | | |160| |
|Tyr|Val|Lys|His|Pro|Phe|Asp|Thr|Pro|Met|Gly|Val|Glu|Gly|Glu|Asp|
| | | |165| | | |170| | | | |175| | |
|Glu|Asp|Glu|Asp|Ala|Asp|Ile|Tyr|Asp|Ser|Glu|Asp|Tyr|Asp|Leu|Thr|
| | |180| | | |185| | | | |190| | | |
|Pro|Asp|Glu|Asp|Glu|Ile|Ile|Gly|Asp|Asp|Met|Asp|Asp|Leu|Asp|Asp|
| |195| | | |200| | | | |205| | | | |
|Glu|Glu|Glu|Glu|Glu|Val|Arg|Ile|Glu|Glu|Val|Gln|Glu|Glu|Asp|Glu|
|210| | | |215| | | | |220| | | | | |
|Glu|Asp|Asn|Asp|Gly|Glu|Glu|Glu|Gln|Glu|Glu|Glu|Glu|Glu|Glu|Glu|
|225| | | |230| | | | |235| | | | | |240|
|Gln|Lys|Glu|Glu|Val|Lys|Pro|Glu|Pro|Lys|Lys|Ser|Lys|Lys|Glu|Lys|
| | | |245| | | |250| | | | |255| | |
|Lys|Arg|Lys|His|Glu|Glu|Lys|Glu|Glu|Glu|Lys|Lys|Ala|Lys|Lys|Val|
| | |260| | | |265| | | | |270| | | |
|Lys|Lys|Val|Glu|Phe|Lys|Lys|Asp|Leu|Glu|Glu|Gly|Pro|Thr|Lys|Pro|
| |275| | | |280| | | | |285| | | | |
|Lys|Ser|Lys|Lys|Glu|Gln|Asp|Lys|His|Lys|Pro|Lys|Ser|Lys|Val|Leu|
|290| | | |295| | | |300| | | | | | |
|Glu|Gly|Gly|Ile|Val|Ile|Glu|Asp|Arg|Thr|Ile|Gly|Asp|Gly|Pro|Gln|
|305| | | |310| | | |315| | | | | |320| |
|Ala|Lys|Arg|Gly|Ala|Arg|Val|Gly|Met|Arg|Tyr|Ile|Gly|Lys|Leu|Lys|
| | | |325| | | |330| | | | |335| | |
|Asn|Gly|Lys|Val|Phe|Asp|Lys|Asn|Thr|Ser|Gly|Lys|Pro|Phe|Ala|Phe|
| | |340| | | |345| | | | |350| | | |
|Lys|Leu|Gly|Arg|Gly|Glu|Val|Ile|Lys|Gly|Trp|Asp|Ile|Gly|Val|Ala|
| |355| | | |360| | | | |365| | | | |
|Gly|Met|Ser|Val|Gly|Gly|Glu|Arg|Arg|Ile|Ile|Ile|Pro|Ala|Pro|Tyr|
|370| | | |375| | | | |380| | | | | |
|Ala|Tyr|Gly|Lys|Gln|Ala|Leu|Pro|Gly|Ile|Pro|Ala|Asn|Ser|Glu|Leu|
|385| | | |390| | | |395| | | | | |400|
|Thr|Phe|Asp|Val|Lys|Leu|Val|Ser|Met|Lys|Asn|
| | | |405| | | |410| | | |